(12) United States Patent
Hill et al.

(10) Patent No.: US 11,547,492 B2
(45) Date of Patent: Jan. 10, 2023

(54) MECHANICAL MODULES OF CATHETERS FOR SENSOR FUSION PROCESSES

(71) Applicant: St. Jude Medical International Holding S.à.r.l., Luxembourg (LU)

(72) Inventors: Anthony D. Hill, Minneapolis, MN (US); Cable Thompson, St. Paul, MN (US); Yuriy Malinin, Edina, MN (US); Paul Belk, Maple Grove, MN (US); Eric Lundquist, Annandale, MN (US); Maxim Yoresh, Haifa (IL)

(73) Assignee: ST JUDE MEDICAL INTERNATIONAL HOLDING, SA.R.L., Luxembourg (LU)

(*) Notice: Subject to any disclaimer, the term of this patent is extended or adjusted under 35 U.S.C. 154(b) by 716 days.

(21) Appl. No.: 16/667,070

(22) Filed: Oct. 29, 2019

(65) Prior Publication Data
US 2020/0138525 A1  May 7, 2020

Related U.S. Application Data

(60) Provisional application No. 62/756,915, filed on Nov. 7, 2018.

(51) Int. Cl.
| A61B 34/20 | (2016.01) |
| A61B 18/14 | (2006.01) |
| A61B 5/00 | (2006.01) |
| A61B 5/06 | (2006.01) |

(Continued)

(52) U.S. Cl.
CPC .............. *A61B 34/20* (2016.02); *A61B 5/065* (2013.01); *A61B 5/6852* (2013.01); *A61B 18/1492* (2013.01); *A61B 2018/00875* (2013.01); *A61B 2034/2051* (2016.02); *A61B 2034/301* (2016.02)

(58) Field of Classification Search
CPC ..... A61B 5/065; A61B 5/0538; A61B 5/1495; A61B 2034/102; A61B 5/6852; A61B 5/068; A61B 5/063; A61B 18/1492
See application file for complete search history.

(56) References Cited

U.S. PATENT DOCUMENTS

| 6,233,476 B1 | 5/2001 | Strommer et al. |
| 7,197,354 B2 | 3/2007 | Sobe |
| 7,263,397 B2 | 8/2007 | Hauck et al. |

(Continued)

*Primary Examiner* — Jon Eric C Morales
(74) *Attorney, Agent, or Firm* — Billion & Armitage

(57) ABSTRACT

Systems and methods are described for implementing a catheter model to estimate shape of a deformable catheter in a three-dimensional space. The catheter model includes two or more model segments that correspond to two or more segments of the deformable catheter. Each model segment includes a length and location of model electrode(s) and/or model magnetic sensor(s) corresponding electrodes and/or magnetic sensors of the deformable catheter. Variable shape parameter define a curvature of the segment. Varying the shape parameters generates a plurality of potential catheter shapes. In conjunction with generating the potential catheter shapes, impedance and/or magnetic responses (e.g., measured responses) are obtained for the physical electrodes and/or physical magnetic sensors of the deformable catheter. Using a selected one (e.g., most likely) of the potential catheter shapes and the measured responses, the shape parameters are updated and a catheter shape is generated and displayed.

20 Claims, 17 Drawing Sheets

(51) Int. Cl.
 *A61B 34/30* (2016.01)
 *A61B 18/00* (2006.01)

(56) References Cited

U.S. PATENT DOCUMENTS

| | | |
|---|---|---|
| 7,386,339 B2 | 6/2008 | Strommer et al. |
| 2007/0060833 A1 | 3/2007 | Hauck |
| 2013/0066193 A1 | 3/2013 | Olson et al. |
| 2020/0138330 A1* | 5/2020 | Thompson ............. A61B 34/20 |
| 2020/0138334 A1* | 5/2020 | Hill ...................... A61B 5/6852 |
| 2020/0138525 A1* | 5/2020 | Hill ...................... A61B 5/0044 |

\* cited by examiner

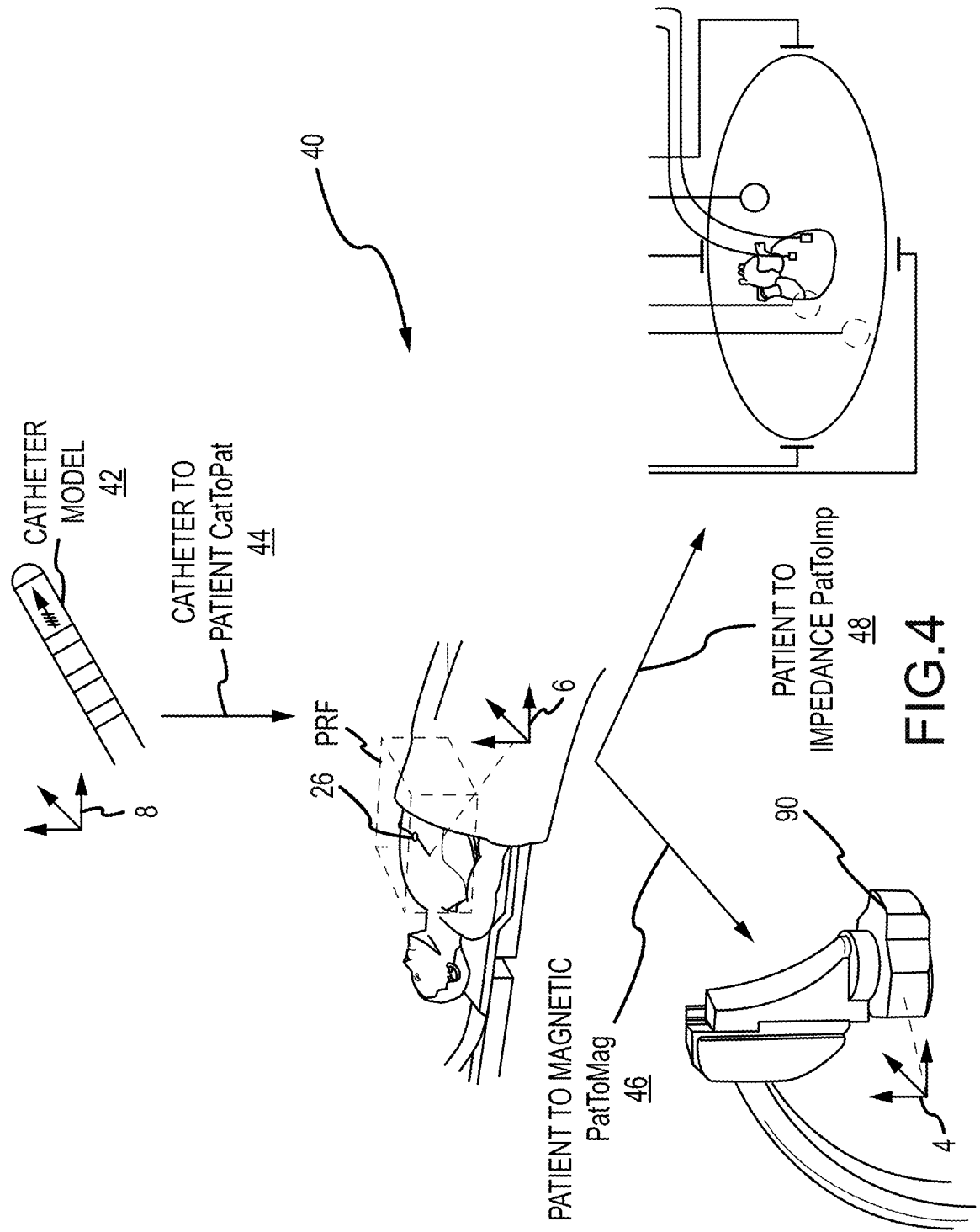

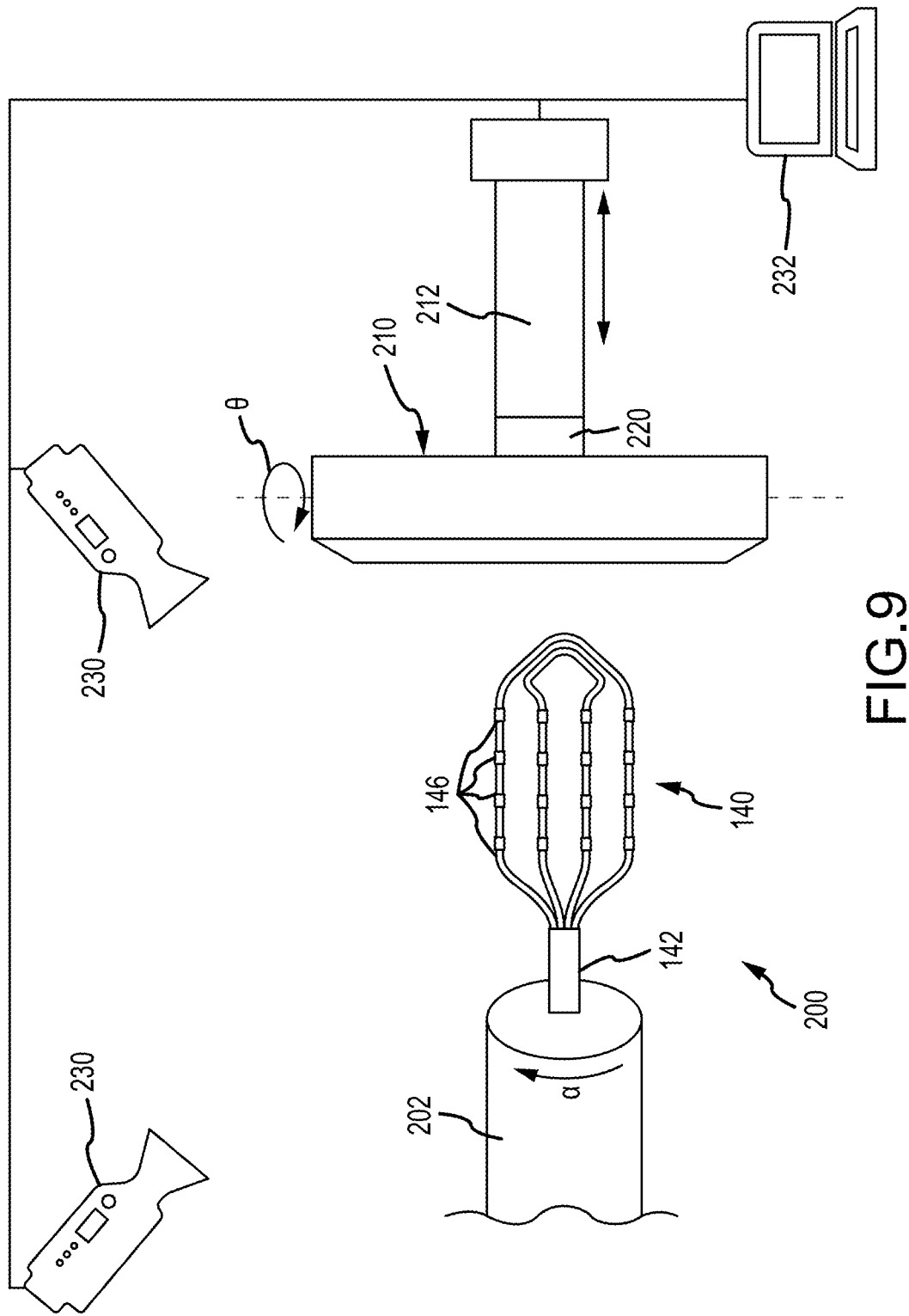

MECHANICAL MODULES OF CATHETERS FOR SENSOR FUSION PROCESSES

CROSS REFERENCE

The present application claims the benefit of the filing date of U.S. Provisional Application No. 62/756,915 having a filing date of Nov. 7, 2018, the entire contents of which is incorporated herein by reference.

BACKGROUND a. Field

The present disclosure relates generally to locating a medical device in a patient reference frame using a medical device model that estimates the shape of a medical device and updated the shape of the model using measurements from impedance electrodes and magnetic sensors of the medical device.

b. Background

Various systems are known for determining the position and orientation (P&O) of a medical device in a human body, for example, for visualization and navigation purposes. One such system is known as an electrical impedance-based positioning system. Electrical impedance-based systems generally include one or more pairs of body surface electrodes (e.g., patches) outside a patient's body, a reference sensor (e.g., another patch) attached to the patient's body, and one or more sensors (e.g., electrodes) attached to the medical device. The pairs can be adjacent, linearly arranged, or associated with respective axes of a coordinate system for such a positioning system. The system can determine P&O by applying a current across pairs of electrodes, measuring respective voltages induced at the device electrodes (i.e., with respect to the reference sensor), and then processing the measured voltages.

Another system is known as a magnetic field-based positioning system. This type of system generally includes one or more magnetic field generators attached to or placed near the patient bed or other component of the operating environment and one or more magnetic field detection coils coupled with a medical device. Alternatively, the field generators may be coupled with a medical device, and the detection coils may be attached to or placed near a component of the operating environment. The generators provide a controlled low-strength AC magnetic field in the area of interest (i.e., an anatomical region). The detection coils produce a respective signal indicative of one or more characteristics of the sensed field. The system then processes these signals to produce one or more P&O readings associated with the coils (and thus with the medical device). The P&O readings are typically taken with respect to the field generators, and thus the field generators serve as the de facto "origin" of the coordinate system of a magnetic field-based positioning system. Unlike an electrical impedance-based system, where the coordinate system is relative to the patient on which the body surface electrodes are applied, a magnetic field-based system has a coordinate system that is independent of the patient.

Both electrical impedance-based and magnetic field-based positioning systems provide advantages. For example, electrical impedance-based systems provide the ability to simultaneously locate (i.e., provide a P&O reading for) a relatively large number of sensors on multiple medical devices. However, because electrical impedance-based systems employ electrical current flow in the human body, such systems may be subject to electrical interference. As a result, geometries and representations that are rendered based on position measurements may appear distorted relative to actual images of subject regions of interest. Magnetic field-based coordinate systems, on the other hand, are not dependent on characteristics of the patient's anatomy and typically provide improved accuracy. However, magnetic field-based positioning systems are generally limited to tracking relatively fewer sensors.

Efforts have been made to provide a system that combines the advantages of an electrical impedance-based positioning system (e.g., positioning of numerous electrodes) with the advantages of a magnetic-field based coordinate system (e.g., independence from patient anatomy, higher accuracy). In an embodiment, such a system may be provided by registering the coordinate systems of an electrical impedance-based positioning system with the coordinate system of a magnetic field-based positioning system. In such an arrangement, locations of electrodes may be identified in an impedance-based coordinate system in conjunction with identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the magnetic-based coordinate system once the transformation is determined. Accordingly, the electrical impedance-based electrodes can be identified in the coordinate system of the magnetic field-based positioning system thereby increasing the positioning accuracy for the electrodes. While providing improved electrode positioning, the determination of a transformation between the impedance-based coordinate system and the magnetic based impedance system and subsequent registration of the electrode locations to the magnetic coordinate system can fail to account for various impedance shifts and/or drifts, associated with the electrode(s).

The previous systems that utilize electrode information (e.g., impedance measurements) and magnetic sensor information to provide improved electrode positioning in three-dimensional space (e.g., within a body of a patient) rely primarily on impedance-based measurements. That is, the magnetic sensor information (e.g., magnetic sensor measurements) delivers additional accuracy. This may be described as an impedance-primary location arrangement. Due to the distortion and temporal instability of the impedance measurements, such an arrangement can suffer from instability. Further, the previous impedance-primary location arrangements, in some instances, fail to account for various errors within the system. Further, such systems may fail to take into account other system inputs (e.g., patient movement, shape of the medical device, etc.), which may affect the calculated locations or positions of the electrodes. In summary, registration of an impedance-based system to magnetic-based system may fail to include additional information which may be observed and/or inferred and which may improve the overall identification of catheter and/or electrode positions in a three-dimensional space.

BRIEF SUMMARY OF THE INVENTION

Various embodiments described herein provide systems, methods and/or non-transitory computer readable medium storing instructions (i.e., utilities) for use in estimating the shape of a deformable catheter in a three-dimensional space (e.g., patient reference space). A catheter model is used to estimate the shape of the deformable catheter. The catheter model includes definitions for two or more model segments that correspond to two or more segments of the deformable catheter. Typically, a length of each model segment is defined as are the location(s) of electrode(s) and/or magnetic sensor(s) along the length. The spacing of the electrodes and/or magnetic sensors in the definition corresponds to the spacing of the physical electrodes and/or magnetic sensors of the corresponding physical catheter (i.e., deformable catheter). Each model segment may have one or more variable shape parameters that define a curvature of the segment. In an arrangement, the model segments each include a variable curvature parameter and a torsional parameter. These parameters may be varied over predetermined ranges that may be predetermined and/or depend on the physical properties of the modeled catheter. Further, the parameters of each model segment may be different. The shape parameters are varied by a computer to generate a plurality of potential catheter shapes. In an arrangement, the potential catheter shapes define a state distribution of potential shapes. In conjunction with generating the potential catheter shapes, impedance and/or magnetic responses (e.g., measured responses) may be obtained for the electrodes and/or magnetic sensors of the deformable catheter disposed in the three-dimensional space. For instance, a medical positioning system may measure these responses. Using a selected one of the catheter shapes and the measured responses, the utility is operative to update the variable shape parameters to more closely fit the catheter model to the shape of the deformable catheter. The updated shape parameters may be used to generate a catheter shape, which may be output to a display. Such updating may be substantially continuous. For instance, the shape parameters and/or a generated catheter shape may be updated 30, 50 or even 100 times per second.

In an arrangement, the selected catheter shape model is used to predict the location of electrodes and/or magnetic sensors in the three-dimensional space. In such an arrangement, the catheter model may be transformed from a catheter reference frame to the three-dimensional space to predict the locations of model electrodes and/or model sensors in the three-dimensional space. Predicted responses are generated for the predicted locations of the model electrodes and/or model sensors. Such predicted responses may be generated by an impedance model that models an impedance field for the three-dimensional space and/or a magnetic model that models a magnetic field of the three-dimensional space. Based on the predicted responses and the measured responses, the utilities may update the locations (e.g., generate calculated locations) of the electrodes or sensors in the three-dimension space. The utilities may utilize information from both the predicted responses and the measured responses to produce the calculated locations for the electrodes and/or sensors of the catheter. The calculated locations typically have an accuracy that is greater than locations produced by either the predicted responses or the measured responses. Further, the predicted responses and measured responses may be utilized to update the variable shape parameters.

In an embodiment, the utilities integrate (e.g., fuse) the predicted and measured responses to estimate hidden variables of the system. Such hidden variables may include a position the catheter in the three-dimensional space as well as the variable parameters of the catheter model. In an arrangement, the variable parameters of the model segments of the catheter model represent state variables of a state vector. Such an arrangement allows updating the various parameters based, in part, on the measured responses of the physical system. In such an arrangement, an estimator system may estimate latent (e.g., hidden) variables to iteratively improve the correspondence of the catheter model with the physical catheter it represents. In an embodiment, the estimator is an extended Kalman filter. In any embodiment utilizing an estimator, a state space estimation of possible states (e.g., catheter shapes) may be generated. A most likely shape may be represented by the mean the state distribution. The mean of the state space estimation may be mapped to measured responses to produce a corrected state space estimation. Calculated locations of the electrodes and/or sensors may be generated from the corrected state space estimation. Likewise, updated shape parameters may be generated from the corrected state space estimation.

In an arrangement, each model segment of the catheter model includes at least one electrode and/or at least one sensor. Such an arrangement ensures that measured responses from corresponding segments of the physical catheter are available for use in adjusting the variable parameters of each model segment. In an arrangement, the model segments are continuous. The continuous model segments may define an entirety of a deformable portion of the catheter. In an arrangement, each model segment is defined as a moving frame. In one particular arrangement, the moving frame is a Frenet Frame.

Various embodiments described herein provide systems and methods for use in determining shape parameters of a deformable catheter. The systems and method apply know forces and orientations to a catheter. Such systems and methods may be implemented in benchtop testing. In an arrangement, a deformable catheter is held at a known roll angle relative to a central axis of the catheter (e.g., the catheter shaft). A movable sled contacts the distal end of the deformable catheter at a known contact angle. The movable sled is advanced a predetermined distance and/or until a predetermined force set point is achieved. At such time, three dimensional locations of electrode and/or magnetic sensors may be obtained (e.g., using three-dimensional imaging). The three-dimensional locations of the electrodes and/or sensors may be correlated to the known force, roll angle and contact angle to determine shape parameters for one or more segments of the catheter for a known displacement. The process may be repeated for multiple permutations of roll angle, contact angle, displacement and/or force to determine a landscape of shape parameters.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 4 illustrates a set of models utilized for describing a composite model in accordance with the disclosure.

FIG. 9 illustrates a testing system for determining shape parameters relative to deformation.

DETAILED DESCRIPTION

Figure 1:
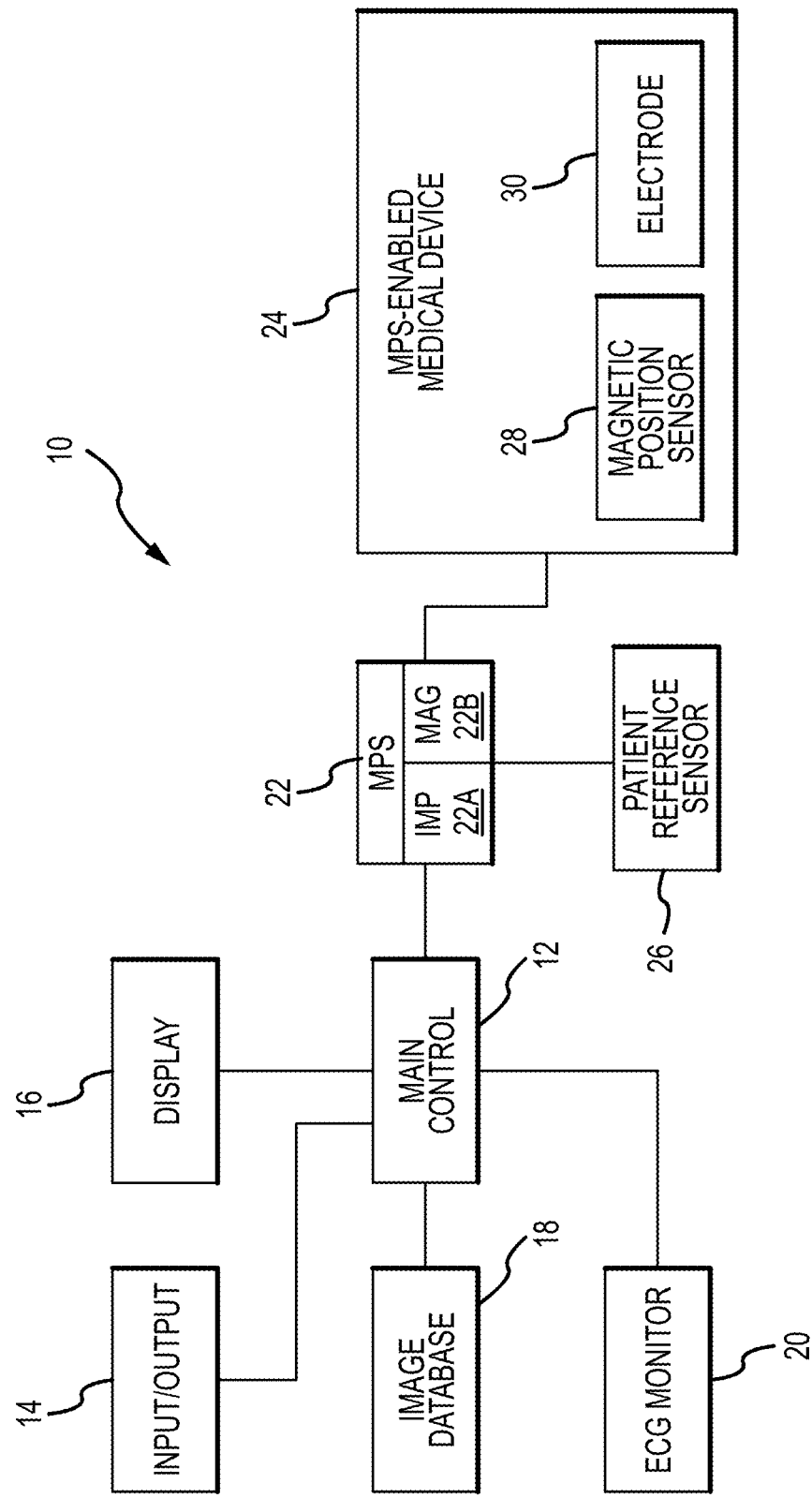
FIG. 1 illustrates depicts a schematic block diagram view of a system for determining the position of a medical device using impedance and magnetic measurements.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating a magnetic position sensor 28 and an electrode 30 may be used.

Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, magnetic position sensor(s) 28 and electrode(s) 30. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Another medical positioning system sensor, namely, patient reference sensor (PRS) 26 can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. PRS 26 can be configured to detect one or more characteristics of the magnetic field in which it is disposed, wherein medical positioning system 22 determines a location reading (e.g., a P&O reading) indicative of the PRS's position and orientation in the magnetic reference coordinate system.

Medical positioning system 22 is configured to serve as the localization system and therefore to determine position (localization) data with respect to one or more magnetic position sensors 28 and/or electrodes 30 and output a respective location reading. In an embodiment, a medical positioning system 22 may include a first medical positioning system or an electrical impedance-based medical positioning system 22A that determines electrode locations in a first coordinate system, and a second medical positioning system or magnetic field-based medical positioning system 22B that determines magnetic position sensors in a second coordinate system. In an embodiment, the location readings may each include at least one or both of a position and an orientation (P&O) relative to a reference coordinate system (e.g., magnetic based coordinate system or impedance based coordinate system). For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Figure 2:
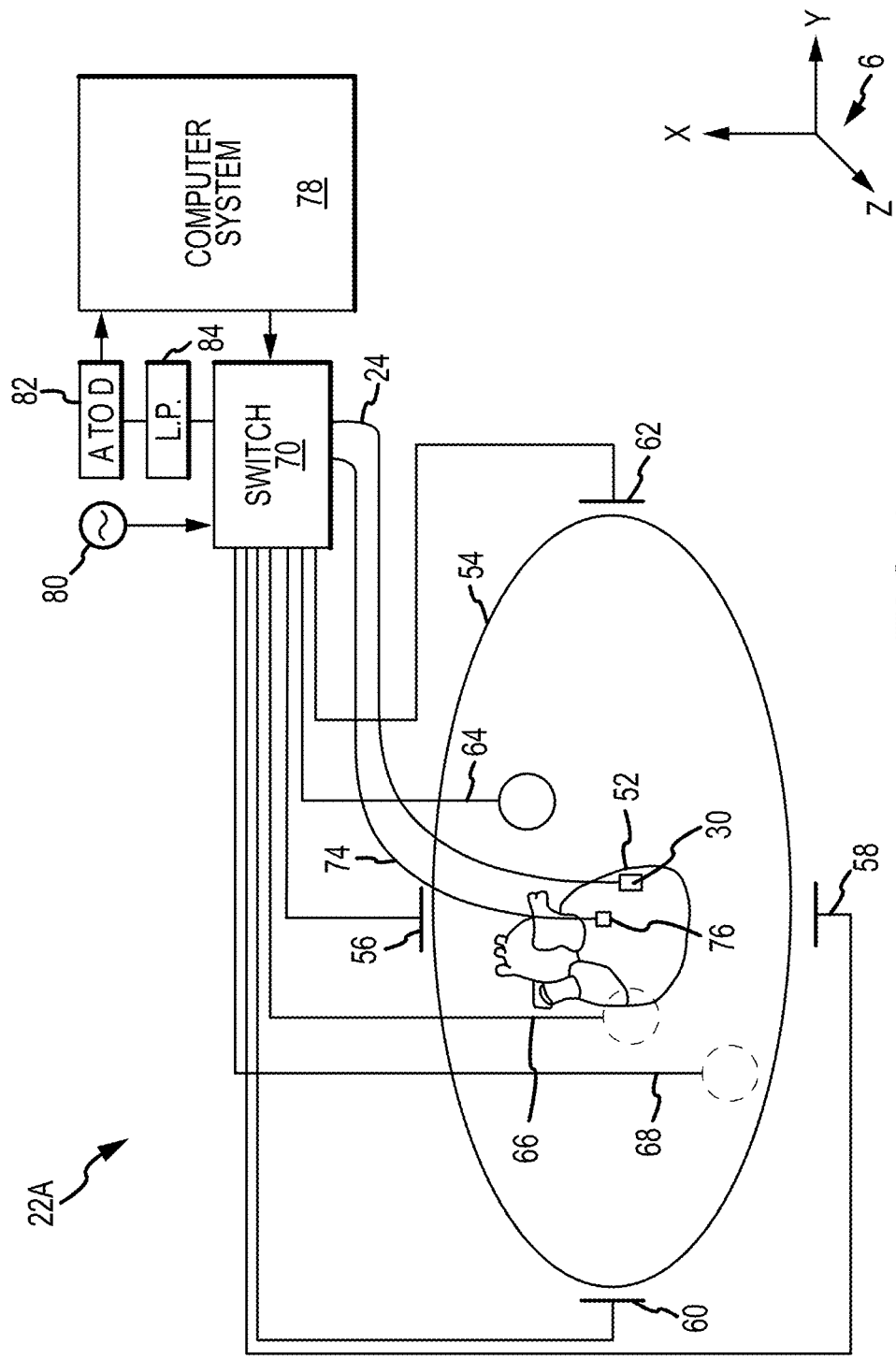
FIG. 2 illustrates a diagrammatic and block diagram view of an embodiment of an electrical impedance-based positioning system.

Impedance based medical positioning system 22A determines electrode locations based on capturing and processing signals received from the electrodes 30 and external electrode patches while the electrodes are disposed in a controlled electrical field (e.g., potential field) generated by the electrode patches, for example. FIG. 2 is a diagrammatic overview of an exemplary electrical impedance-based medical positioning system ('MPS system') 22A. MPS system 22A may comprise various visualization, mapping and navigation components as known in the art, including, for example, an EnSite™ Electro Anatomical Mapping System commercially available from St. Jude Medical, Inc., or as seen generally by reference to U.S. Pat. No. 7,263,397 entitled "Method and Apparatus for Catheter Navigation and Location and Mapping in the Heart" to Hauck et al., or U.S. Patent Publication No. 2007/0060833 A1 to Hauck entitled "Method of Scaling Navigation Signals to Account for Impedance Drift in Tissue", both owned by the common assignee of the present invention, and both hereby incorporated by reference in their entireties.

Medical positioning system 22A includes a diagrammatic depiction of a heart 52 of a patient 54. The system includes the ability to determine a catheter electrode location (i.e., position and orientation) as the catheter distal end is moved around and within a chamber of the heart 52. For this purpose, three sets of body surface electrodes (patches) are shown: (1) electrodes 56, 58 (X-axis); (2) electrodes 60, 62 (Y-axis); and (3) electrodes 64, 66 (Z-axis). Additionally, a body surface electrode ("belly patch") 68 is shown diagrammatically. The surface electrodes are all connected to a switch 70. Of course, other surface electrode configurations and combinations are suitable for use with the present invention, including fewer electrodes, e.g., three electrodes, more electrodes, e.g., twelve, or different physical arrangements, e.g., linear arrangement instead of an orthogonal arrangement.

Medical device 24 is shown as a catheter with a distal electrode 30. Catheter 24 may have additional electrodes in addition to electrode 30 (e.g., a catheter tip electrode and/or ring electrodes) as well as one or more magnetic position sensors (not shown). FIG. 2 also shows a second, independent catheter 74 with a fixed reference electrode 76, which may be stationary on the heart for calibration purposes. It should be understood that catheter 24 may include still other electrodes, and in other embodiments, such as in EP or RF ablation embodiments, the other electrodes may be used for any number of diagnostic and/or therapeutic purposes. For instance, such electrodes and therefore such catheters may be used for performing ablation procedures, cardiac mapping, electrophysiological (EP) studies and other diagnostic and/or therapeutic procedures. Embodiments are not limited to any one type of catheter or catheter-based system or procedure.

FIG. 2 further shows a computer system 78, a signal generator 80, an analog-to-digital converter 82 and a low-pass filter 84. Computer system 78 includes a processing apparatus configured to perform various functions and operations described herein. Computer system 78 may be configured to control signal generator 80 in accordance with predetermined strategies to selectively energize various pairs (dipoles) of surface electrodes. In operation, computer system 78 may (1) obtain raw patch data (i.e., voltage readings) via filter 84 and A-to-D converter 82 and (2) use the raw patch data (in conjunction with electrode measurements) to determine the raw, uncompensated, electrode location coordinates of a catheter electrode positioned inside the heart or chamber thereof (e.g., such as electrode 30) in a three-dimensional coordinate system (e.g., impedance-based coordinate system). Computer system 78 may be further configured to perform one or more compensation and adjustment functions, and to output a location in coordinate system 14 of one or more electrodes such as electrode 72. Motion compensation may include, for example, compensation for respiration-induced patient body movement, as described in U.S. patent application Ser. No. 12/980,515, entitled "Dynamic Adaptive Respiration Compensation with Automatic Gain Control", which is hereby incorporated by reference in its entirety.

Each body surface (patch) electrode is independently coupled to switch 70 and pairs of electrodes are selected by software running on computer system 78, which couples the patches to signal generator 80. A pair of electrodes, for example the Z-axis electrodes 64 and 66, may be excited by signal generator 80 to generate an electrical field in the body of patient 54 and heart 52. In one embodiment, this electrode excitation process occurs rapidly and sequentially as different sets of patch electrodes are selected and one or more of the unexcited (in an embodiment) surface electrodes are used to measure voltages. During the delivery of the excitation signal (e.g., current pulse), the remaining (unexcited) patch electrodes may be referenced to the belly patch 68 and the voltages impressed on these remaining electrodes are measured by the A-to-D converter 82. In this fashion, the surface patch electrodes are divided into driven and non-driven electrode sets. Low pass filter 84 may process the voltage measurements. The filtered voltage measurements are transformed to digital data by analog to digital converter 82 and transmitted to computer 78 for storage under the direction of software. This collection of voltage measurements is referred to herein as the "patch data." The software has access to each individual voltage measurement made at each surface electrode during each excitation of each pair of surface electrodes.

The patch data is used, along with measurements made at electrode 30, to determine a relative location of electrode 30 in what may be termed a patient-based coordinate system or patient reference frame 6. That is, as the patches are applied directly to the patient, the patient defines the reference frame of the impedance measurements. Potentials across each of the six orthogonal surface electrodes may be acquired for all samples except when a particular surface electrode pair is driven (in an embodiment). In one embodiment, sampling while a surface electrode acts as a source or sink in a driven pair is normally avoided as the potential measured at a driven electrode during this time may be skewed by the electrode impedance and the effects of high local current density. In an alternate embodiment, however, sampling may occur at all patches (even those being driven).

Magnetic-based medical positioning system 22B determines magnetic position sensor locations (e.g., P&O) in a magnetic coordinate system based on capturing and processing signals received from the magnetic position sensor 28 while the sensor is disposed in a controlled low-strength alternating current (AC) magnetic (e.g., magnetic) field. Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22B to obtain a respective P&O for the magnetic sensor 28 relative to, for example, a magnetic field generator.

Figure 3:
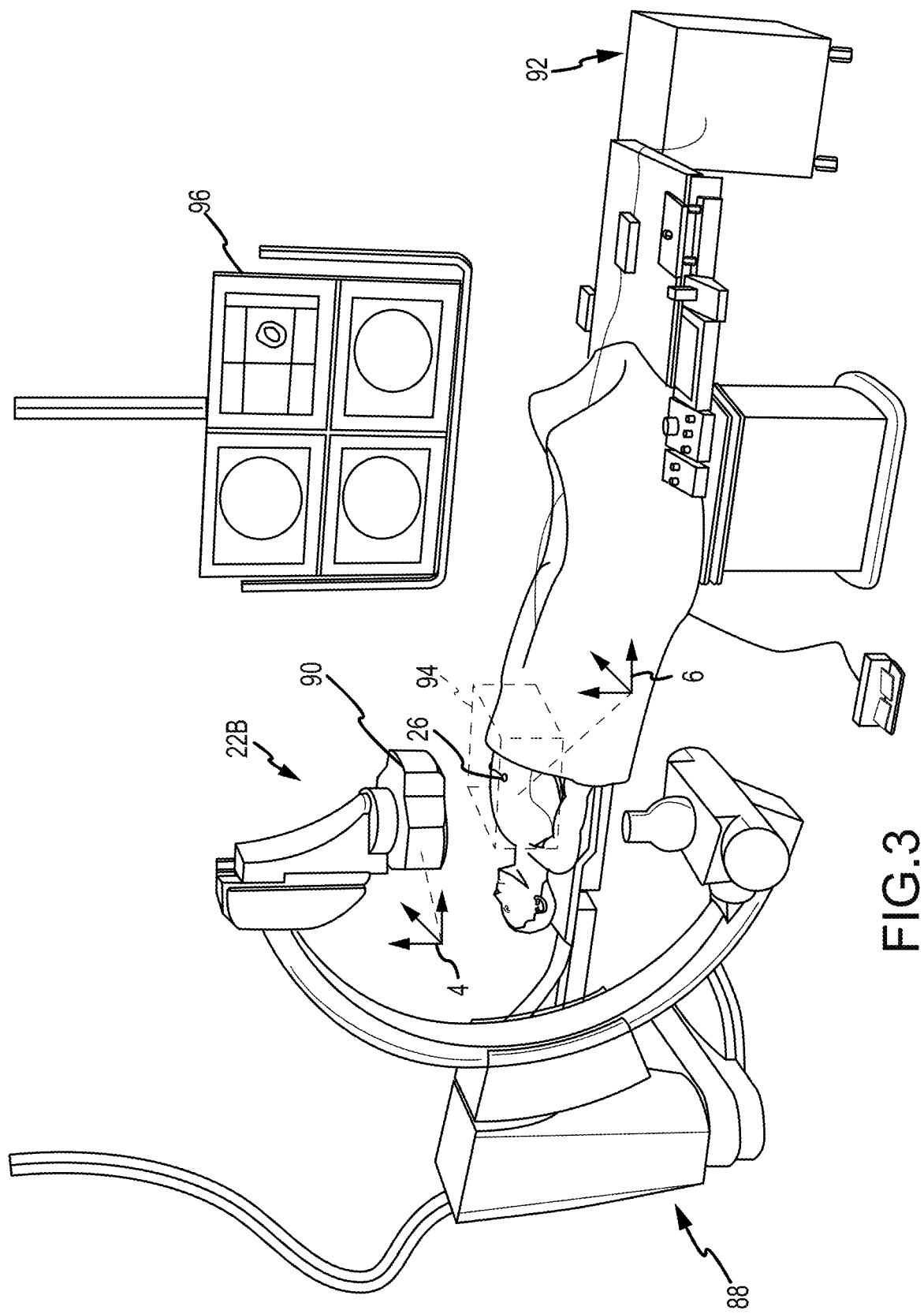
FIG. 3 illustrates an embodiment of a magnetic field-based positioning system.

FIG. 3 is a diagrammatic view of an exemplary magnetic field-based medical positioning system 22B in a fluoroscopy-based imaging environment, designated system 88. A magnetic field generator or magnetic transmitter assembly (MTA) 90 and a magnetic processing core 92 for determining position and orientation (P&O) readings generally define the magnetic field-based positioning system 22B. The MTA 90 is configured to generate the magnetic field(s) in and around the patient's chest cavity in a predefined three-dimensional space designated as motion box 94 in FIG. 4. Magnetic field sensors coupled with device 24 (e.g., catheter or another medical device) are configured to sense one or more characteristics of the magnetic field(s) and, when the sensors are in the motion box 94, each generates a respective signal that is provided to the magnetic processing core 92. The processing core 92 is responsive to these detected signals and is configured to calculate respective three-dimensional position and orientation (P&O) readings for each magnetic field sensor. Thus, the MPS system 22B enables real-time tracking of each magnetic field sensor in three-dimensional space, which forms a magnetic-based coordinate system 4. The position of the sensors may be shown on a display 96 relative to, for example only, a cardiac model or geometry. Additional exemplary embodiments of magnetic field-based medical positioning systems are set forth in co-owned U.S. Pat. No. 7,386,339 and U.S. Pat. App. No 2013/0066193, hereby incorporated by reference in their entirety. It should be understood that variations are possible, for example, as also seen by reference to U.S. Pat. Nos. 7,197,354, and 6,233,476, also hereby incorporated by reference in their entireties. Unlike the electrical impedance-based system discussed in relation to FIG. 2, which has an origin based on a patient reference frame 6 as the body surface electrodes are applied directly to the patient, the origin of the magnetic field-based system is typically based in or on the MTA 90 (e.g., as shown by the dashed line) and is independent of the patient. Stated otherwise, the patient coordinate system (e.g., patient reference frame) 6 and the magnetic-based coordinate system 4 have different origins.

As further illustrated in FIG. 4, a patient reference sensor (PRS) 26 may be applied to the patient. In an embodiment, the PRS 26 may be attached to the patient's manubrium sternum. However other patient locations for the PRS 26 are possible. In an embodiment, the PRS 26 is a magnetic sensor configured to detect one or more characteristics of the magnetic field in which it is disposed, wherein medical positioning system 22B determines a location reading (e.g., a P&O reading) indicative of the position and orientation of the PRS 26 (e.g., in the magnetic-based coordinate system). For the present application, the PRS defines an origin (e.g., PRF 0, 0, 0) in the patient reference coordinate system or patient reference frame 6 (PRF). The origin may be offset from the actual location of the senor. That is, predetermined offsets (e.g., x, y, and z) may be applied to the PRS measurements that correspond with estimated distances between the sensor's placement on the patient and the desired origin. For instance, the origin may be offset from the sensor such that it is within the heart of the patient for cardiac applications. Further, two or more PRS's may be applied to provide additional orientation information for the PRF 6. In any embodiment, as the PRS 26 is attached to the patient and moves with patient movement, the origin of the PRF 6 also moves. Such movement may result from patient respiration and/or physical movements (shifting, rolling etc.) of the patient. The origin of the PRF 6 is thus dependent on the position of the patient and may be updated over time. More specifically, a measurement of the PRS may be determined in the magnetic field coordinate system and this measurement may be utilized as the origin (e.g., with adjustment) of the PRF.

As previously noted, the impedance-based medical positioning systems and magnetic-based medical positioning systems have different strengths and weaknesses. For instance impedance-based systems provide the ability to simultaneously locate a relatively large number of electrodes. However, because impedance-based systems employ electrical current flow in the human body, the system can be subject to measurement inaccuracies due to shift and/or drift caused by various physiological phenomena (e.g., local conductivity changes, sweat/patch interactions, etc.). Additionally, impedance-based systems may be subject to electrical interference. As a result, electrode locations, renderings, geometries and/or representations based on such impedance-based measurements may be distorted. Magnetic-based systems, on the other hand, are not dependent on the characteristics of a patient's anatomy and are considered to provide a higher degree of accuracy. However, magnetic position sensors generally are limited to tracking relatively fewer sensors.

Previous efforts have been made to provide a system that combines the advantages of an electrical impedance-based positioning system (e.g., positioning of numerous electrodes) with the advantages of a magnetic-field based coordinate system (e.g., independence from patient anatomy, higher accuracy). In an embodiment, such a system may be provided by registering the coordinate systems of an electrical impedance-based positioning system with the coordinate system of a magnetic field-based positioning system. In such an arrangement, locations of electrodes may be identified in an impedance-based coordinate system in conjunction with the identifying the locations of one or more magnetic sensors in a magnetic-based coordinate system. In an embodiment, at least a portion of the electrodes and magnetic sensors may be co-located to define fiducial pairs. This co-location allows for determining a transformation (e.g., transformation matrix) between the coordinate systems. The transformation may be applied to the locations of any electrode to register these locations in the magnetic-based coordinate system once the transformation is determined. Accordingly, the electrical impedance-based electrodes can be identified in the coordinate system of the magnetic field-based positioning system thereby increasing the positioning accuracy for the electrodes. Such a system is set forth in co-owned U.S. Pat. Pub. No. 2013/0066193. The previous efforts that utilize electrode information (e.g., impedance measurements) and magnetic sensor information to provide improved electrode positioning in three-dimensional space (e.g., within a body of a patient), in some instances, fail to account for various errors within the system. By way of example, a transformation between the impedance-based coordinate system and the magnetic-based impedance system may underestimate error or uncertainty in the electrode and/or magnetic sensor measurements. Further, registration of an impedance-based system to magnetic-based system may fail to include additional information which may be observed and/or inferred and which may improve the overall identification of catheter and/or electrode positions in a three-dimensional space.

To provide an improved system for determining the location of electrodes in three-dimensional space such as within a body of a patient, the present disclosure is in part directed to a location arrangement (e.g., sensor fusion process or algorithm) that continuously integrates (e.g., fuses) impedance measurements from the electrodes and external patches with position and orientation measurements from magnetic sensors to estimate the latent state (e.g., position) of a medical device disposed within a patient reference frame. The latent state is used to track catheter electrodes within a body of a patient as though there were a magnetic sensor located at each catheter electrode, thereby achieving both accuracy and stability. More broadly, the presented arrangement expands the number of observed parameters utilized to locate the electrodes within a patient reference frame without relying on direct transformation between the impedance-based coordinate system and the magnetic-based impedance coordinate system based on the existence of fiducial pairs of electrodes and sensors. Rather, the impedance measurements and magnetic measurements are utilized as inputs to an overall system model that estimates/predicts and updates catheter electrode locations in a patient reference frame.

FIG. 4 illustrates an embodiment of independent models that are used to mathematically define a catheter and/or electrode location system model. That is, the independent models define a composite model 40 of the system (e.g., in a patient reference frame). The illustrated embodiment of the composite system model 40 includes four models: a catheter model 42 (e.g., medical device model) that predicts the shape (e.g., catheter configuration) of a catheter having one or more electrodes and/or magnetic sensors in a catheter reference frame 8, a catheter position and orientation model 44 that transforms the catheter model from the catheter reference frame 8 into the patient reference frame 6 based on a unique transformation that is specific to the catheter, a magnetic model 46 that predicts magnetic sensor measurements in the patient reference frame, and an impedance model 48 that predicts electrode impedance measurements in the patient reference frame. Each model mathematically describes a portion of the overall system. The catheter model 42 predicts the shape of a physical catheter disposed within the patient body as well as the location of the electrodes and sensors of the physical catheter.

Figure 5A:
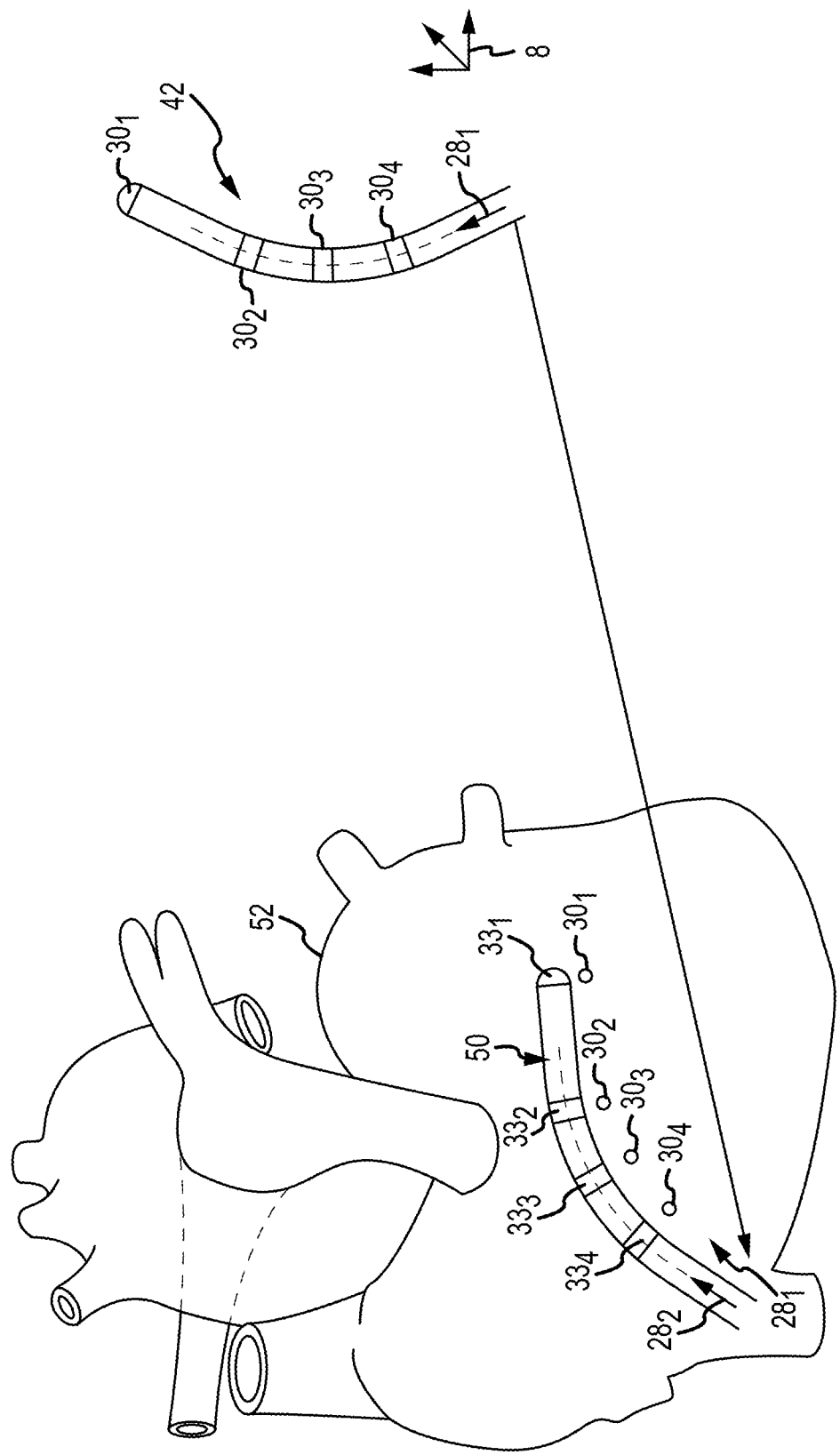
FIG. 5A illustrates a prediction of a catheter shape and translation of the catheter shape to a patient reference frame.
Figure 5B:
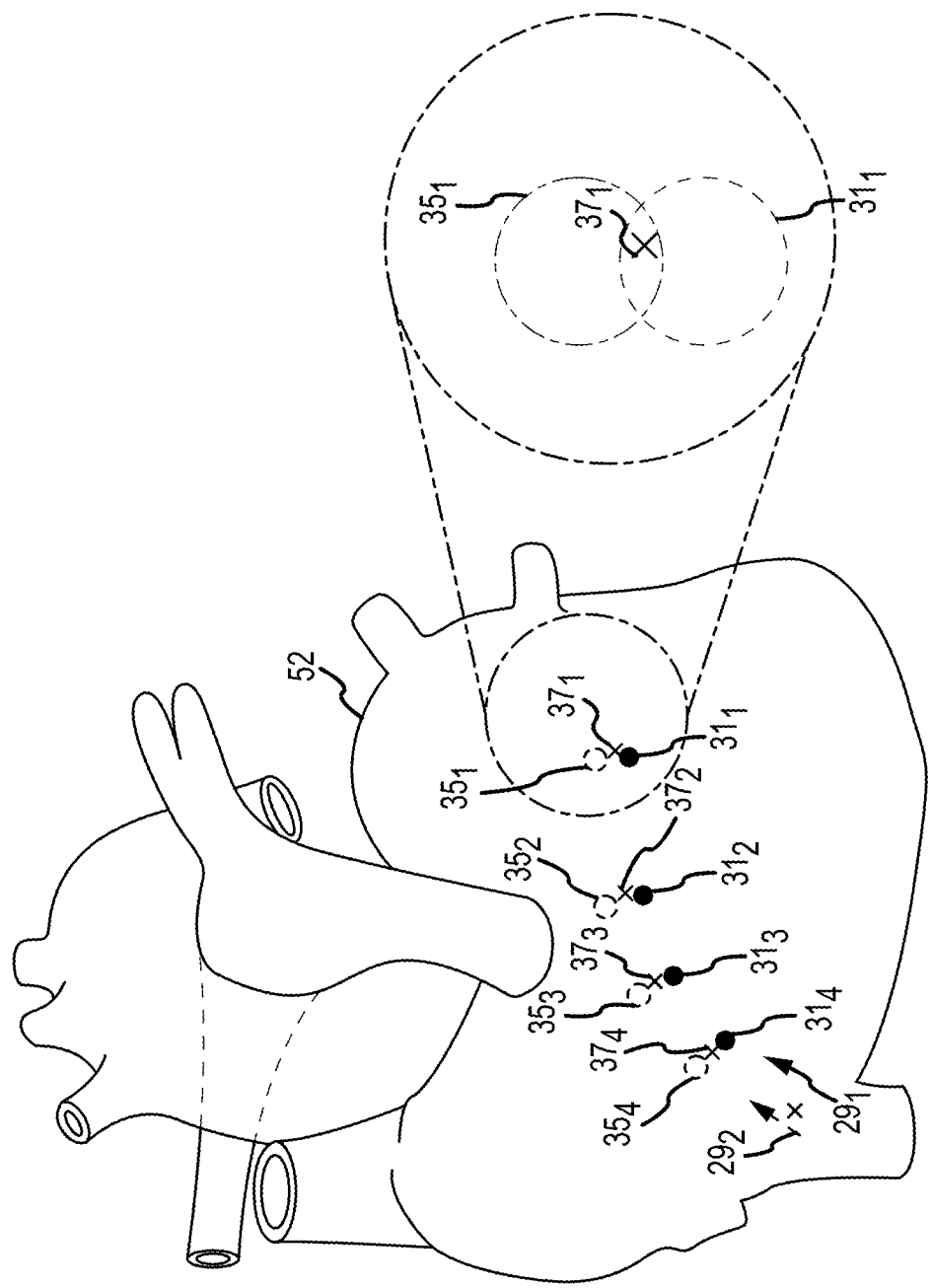
FIG. 5B illustrates the prediction of measurements for predicted locations in a patient reference frame and observed measurements in the patient reference frame.

FIG. 5A further illustrates the cooperation of the various models. Initially, the catheter model 42 predicts a catheter shape of a corresponding physical catheter 50 disposed within a three-dimensional space such as a body of a patient (e.g., heart 52), where the physical catheter has a set of electrode $33_1$-$33_4$ and a magnetic sensor $28_2$. In the illustrated embodiment, the catheter shape includes model positions or locations of electrodes $30_1$-$30_4$ and a magnetic sensor $28_1$ in the catheter reference frame 8. A position and orientation model 44 applies one or more transformations to the catheter model 42 to translate the model from the catheter reference frame 8 to the patient reference frame 6. Upon transformation, locations of the model electrodes $30_1$-$30_4$ and/or model magnetic sensor $28_1$ are predicted in the patient reference frame 6, as illustrated by the solid circles for the electrodes $30_1$-$30_4$ and the vector for the magnetic sensor $28_1$. The impedance model 48 predicts impedance measurements for the predicted electrode locations in the patient reference frame while the magnetic model 46 predicts magnetic measurement for the predicted magnetic sensor location in the patient reference frame. This is illustrated in FIG. 5B where the predicted electrode measurements $31_1$-$31_4$ for each predicted location are represented by solid dots and the predicted magnetic measurement/location $29_1$ is represented by the solid vector. The impedance-based medical positioning system measures responses $33_1$-$33_4$ (e.g., observed measurements) of the physical electrodes $31_1$-$31_4$ within the patient body (e.g., patient reference frame) to an applied potential field to determine locations of the electrodes, as represented the dashed circles. If utilized, the magnetic-based medical positioning system measures the location $29_2$ of the magnetic sensor in the patient body, as represented by the dashed vector. As shown by the magnified portion of FIG. 5B, measured responses of the physical electrode(s) (e.g., $35_1$) and/or sensor(s) (not shown) and the predicted responses of the electrode (e.g., $31_1$) and/or sensors (not shown) each contain some unknown error or noise (e.g., uncertainty). In an embodiment, the uncertainty of the measured responses and predicted responses may partially overlap. The predicted measurements and the observed measurements are then utilized to predict true (e.g., updated) or calculated locations of the electrodes $37_1$-$37_4$ as represented by the X's in FIG. 5B. As shown in the magnified portion of FIG. 5B, the calculated location $37_1$ may reside in the overlap of the predicted response location and the measured response location. In any embodiment, the calculated locations typically have a higher accuracy than locations resulting from either the predicted responses or the observed responses. The calculated locations may then be output to a display. See, e.g., FIG. 1. That is, an updated representation of a catheter or other medical device may be output or rendered to the display using the calculated locations.

Catheter Models

In an embodiment, the present disclosure describes techniques for parameterizing the shapes of deformable catheters to define catheter models, which predict the shapes of catheters. The disclosure also describes a technique for determining the likelihood of a set of shape parameters and resulting shape predicted by a catheter model. Each catheter model describes the physical/mechanical parameters of a specific deformable catheter to predict a potential shape of the catheter, which may be projected into a patient reference frame (e.g., a three dimensional space). Initially, the predicted shape is in a catheter reference frame. Accordingly, once the shape of the catheter is predicted by the catheter model, that model shape may be transformed into a patient reference frame to predict locations of electrodes and/or magnetic sensors of the physical catheter within a patient reference frame (e.g., patient body or three-dimensional space). In the case of the electrodes, impedance measurements may be predicted based on the predicted locations of the electrodes. Such predicted impedance measurements may be utilized with observed noisy measurements of the electrodes of the physical catheter (e.g., within the three-dimensional space) to calculate locations of the electrodes in the three-dimensional space (e.g., patient reference frame). Further, the predicted impedance measurement and observed measurement may be utilized to adjust or update one or more parameters of the catheter model to better fit a current shape of the physical catheter.

Each catheter model is specific to the physical and mechanical parameters of a specific catheter. Along these lines, each catheter model mathematically defines a specific physical catheter and includes a set of numerical parameters (e.g., set of shape parameters), which together describe the shape of the catheter at a given moment and allow derivation of all electrode and/or sensor locations. In an embodiment, the physical catheter is described as having two or more segments having known known lengths with electrodes and/or sensors disposed at locations along the length of each segment. Corresponding catheter model segments are defined having corresponding lengths. Further locations of the electrode and/or magnetic sensors of the physical catheter are defined along the lengths of the model segments. Each model segment includes at least a first variable parameter that describe the shape of the model segment. Further, altering these parameters allows for altering the shape of the model segment. In an embodiment, the shape parameters of the model segments permit the reproduction of any physically feasible shape of the catheter. In a further embodiment, the shape may be continuous as a function of each shape parameter. In a yet further embodiment, the predicted shape may be smoothed as a function of each shape parameter. In any embodiment, it is desirable that the total number of shape parameters be reduced while still permitting accurate prediction of a catheter shape as increasing numbers of parameters impairs computational performance and/or stability. In an embodiment, the shape parameters of the catheter models are variables (e.g., state variables) of a stochastic process. In such an embodiment, a state distribution of the shape parameters may define potential shapes of the catheter. A most likely shape of the state distribution (e.g., mean of the state distribution) may be transformed into a patient reference frame utilizing one or more transformations (e.g., catheter transformation(s)). In an embodiment, the transformation is a rigid transformation that preserves shape and size of the catheter model. For example, a six degree of freedom rigid-body translation may be applied to translate the catheter shape model into the patent reference frame.

In an embodiment, modeling a catheter includes dividing the catheter into a number of continuous segments. Each corresponding model segment is described with a moving frame (e.g., Frenet frame) following the arc of the model segment. This allows determining the position of numerous electrodes along the arc of the model segment with a small number of degrees of freedom. In an embodiment, the moving-frame formulation preserves inter-electrode distances through the entire domain of the parameter space, while also allowing for the reproduction of physically realistic catheter kinematics.

Figure 6:
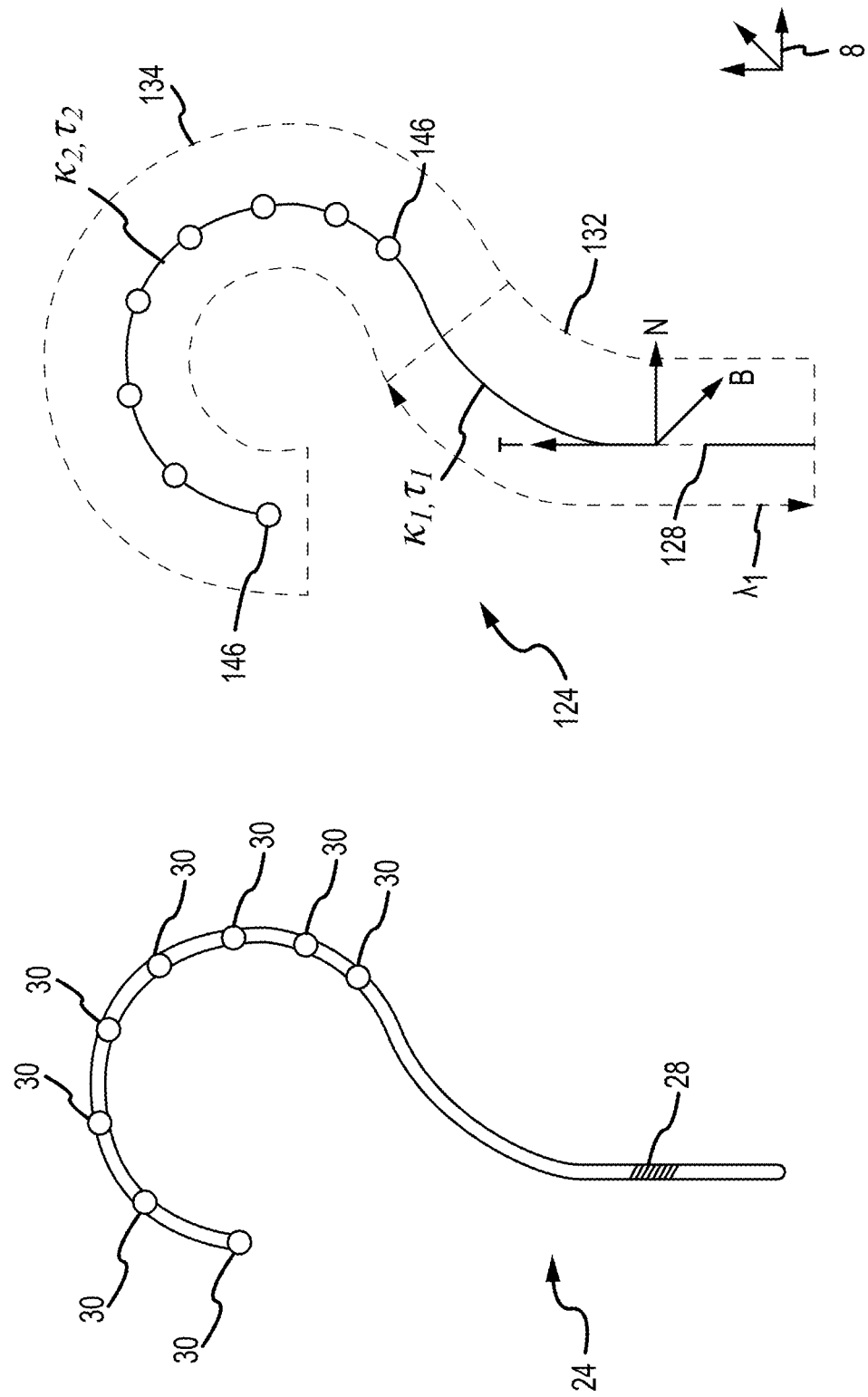
FIG. 6 illustrates a physical catheter and a corresponding catheter shape model.

FIG. 6 illustrates one embodiment of a deformable physical catheter 24 and corresponding catheter shape model 124. The deformable catheter 24 includes a single catheter spline, a plurality of electrodes 30 and a magnetic sensor 28. The catheter model, in the present embodiment, divides the spline into two model segments, a proximal shaft segment 132 and a distal hoop segment 134. Each segment 132, 134 is described by a moving Frenet frame of constant parameters that follows an arc of the corresponding segment of the physical catheter. Model electrodes 146 are located on distal hoop model segment 134 according to mechanical specifications. For example, the position of each electrode may be defined by its distance or length l along the length $\lambda$ of Frenet frame (e.g., from an origin of the frame). In the present embodiment, all electrodes are shown as being located on the distal hoop segment 134, however, it will be appreciated that each model segment may include electrodes, depending on the physical configuration of the physical catheter 24. In the present embodiment, the proximal shaft model segment 132 includes a single model magnetic sensor 128. Again, it will be appreciated that each model segment may include one or more magnetic sensors and/or one or more electrodes. The parameterization of the model segments thus fully describes the electrode locations in a catheter reference frame 8 of the catheter model 124.

Frenet formulas describe the geometric properties of a continuous, differentiable curve in three-dimensional space. More specifically, the Frenet formulas describe the derivatives of the tangent 'T', normal 'N', and binormal 'B' unit vectors in terms of one other along at each point along the length $\lambda$ of the frame. See FIG. 6. The tangent, normal, and binormal unit vectors, or collectively the Frenet frame are defined where T is the unit vector tangent to the curve, pointing in the direction of motion, N is the normal unit vector, the derivative of T with respect to the arc length parameter of the curve, divided by its length and B is the binormal unit vector, which is the cross product of T and N. The Frenet Formulas are:

$$\frac{dT}{ds} = \kappa N$$

$$\frac{dN}{ds} = -\kappa T + \tau B$$

$$\frac{dB}{ds} = -\tau N$$

where d/ds is the derivative with respect to arc length, $\kappa$ is the curvature (e.g., inverse or radius of a curve), and $\tau$ is the torsion of the curve. The two scalars $\kappa$ and $\tau$ effectively define the curvature and torsion of a curve. For each segment in a homogenous coordinate system, the Frenet frame ($F_F$) for a curve defined by $\kappa$ and $\tau$ at a distance $\lambda$ along the curve is defined as:

$$F_F = \begin{bmatrix} 0 & \kappa & 0 & 0 \\ -\kappa & 0 & \tau & 0 \\ 0 & -\tau & 0 & 0 \\ 0 & 0 & 0 & 0 \end{bmatrix} \lambda$$

Utilization of the Frenet frame effectively permits defining each model segment utilizing two parameters curvature $\kappa$ and torsion $\tau$.

In the embodiment of FIG. 6, the catheter shape model includes two continuous curves (e.g., model segments) of constant curvature and torsion rotated 90 degrees from one another. The first curve represents the bend between the proximal shaft segment 132 and the distal hoop segment 134. The first curve is defined by $\kappa_1$ and torsion $\tau_1$. The second curve represents the distal hoop segment 134. The second curve is defined by $\kappa_2$ and torsion $\tau_2$. Thus, the catheter shape model 124 is defined by four parameters: two curvatures and two torsions, which define all possible shapes that the catheter model may take. These parameters each typically have a predetermined or experimentally determined numerical range (e.g., from a corresponding physical catheter). Further, the curve parameters typically form state variables in a stochastic process that predicts potential shapes of the catheter model. Locations of model electrode and/or magnetic sensors may be derived by their known locations along their respective frame for a given model.

In an embodiment, state transition models (e.g., matrixes), which apply the effect of each curve parameter at time k−1 to the curve parameters at time k are as follows:

$$f(x)_i = \kappa_{i(k-1)} + \textit{f}_{\textit{i-curve}}(\hat{\kappa}_i - \kappa_{i(k-1)})$$

$$f(x)_i = \tau_{i(k-1)} + \textit{f}_{\textit{i-torsion}}(\hat{\tau}_i - \tau_{i(k-1)})$$

where:

i represents the curve segment (e.g., i=1 or 2 in the present embodiment);

$\hat{k}$ represents a default curvature for each curve segment;

$\hat{t}$ represents a default torsion for each curve segment; and $\hat{f}$ represents a matrix defining the forcing factors for each curve parameter.

The transition matrix when applied, varies each of the state variables to generate a plurality of possible catheter shapes. In an embodiment, this produces a state distribution of possible catheter shapes. See FIG. 7A. Typically, the mean of the state distribution represents the most likely catheter shape and corresponding set of catheter parameters.

In an embodiment, the forcing factor(s) may be derived from catheter specific mechanical parameters. In an embodiment, the forcing factor may represent the returning force of a shape metal wire that forms the spline of the catheter. In such an embodiment, the forcing factor F applies a returning force to a deformation associated with the given shape parameters that represents the force applied by the shape metal wire attempting to return to an un-deformed or nominal state from a current shape parameter. In an embodiment for a single-segment catheter which is nominally straight and untwisted with the same torsional stiffness as the rotational stiffness:

$$\text{let } x_k = \begin{bmatrix} \kappa_{1(k)} \\ \tau_{1(k)} \end{bmatrix}$$

$$F = \begin{bmatrix} 1-\hat{f}_1 & 0 \\ 0 & 1-\hat{f}_1 \end{bmatrix} = \begin{bmatrix} 0.99 & 0 \\ 0 & 0.99 \end{bmatrix}$$

$$x_{default} = \begin{bmatrix} \hat{k}_1 \\ \hat{t}_1 \end{bmatrix} = \begin{bmatrix} 0 \\ 0 \end{bmatrix}$$

$$x_k = f(x_{k-1}) = Fx_{k-1} + x_{default}\hat{f}_1$$

As will be appreciated, such a forcing factor F is unique for a specific catheter. The inclusion of the forcing factor prevents the state transition model from being identity to a prior state.

Figure 7A:
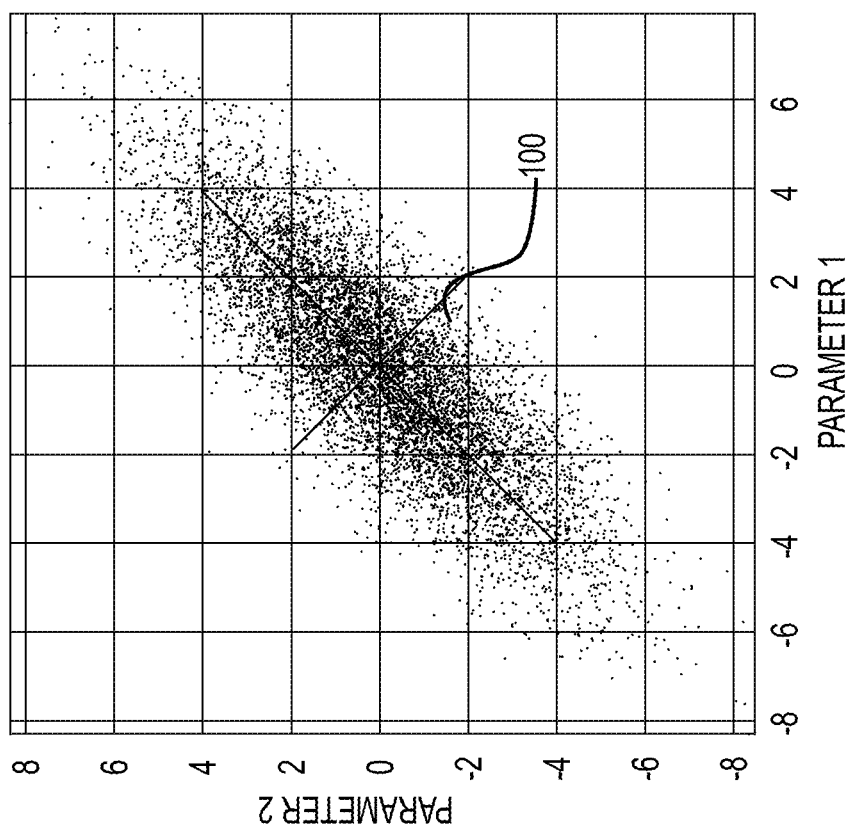
FIGS. 7A-7C illustrate a state distribution, a regularizing function and application of the regularizing function to the state distribution.

Through application of the above noted transition models, a state distribution of potential catheter shapes, in the catheter frame of reference, may be estimated for time k. FIG. 7A illustrates one such distribution. Based on the most likely shape (e.g., the mean of the distribution), the locations of the model electrodes may be determined in the catheter frame of reference.

An observational model may be implemented to map the state parameters into a physical domain (e.g., catheter frame of reference). In an embodiment, this is performed by evaluating the matrix exponential for the Frenet Frame. In an embodiment, the matrix exponential is an integrated differential matrix with constant terms (e.g., curvature and torsion) over the arc length for all electrodes where the position l of the electrodes varies over the arc length. In an embodiment, the matrix evaluation may be computed using a Givens rotation and trigonometric functions.

In an embodiment, a Given's rotation is initially computed to eliminate two terms of the Frenet Frame:

$$\theta = \sqrt{\kappa^2 + \tau^2}$$

such that:

$$G(\kappa, \tau) = \begin{bmatrix} \frac{\kappa}{\theta} & 0 & \frac{\tau}{\theta} & 0 \\ 0 & 1 & 0 & 0 \\ \frac{-\tau}{\theta} & 0 & \frac{\kappa}{\theta} & 0 \\ 0 & 0 & 0 & 1 \end{bmatrix}$$

After expanding the first several terms of the remaining matrix exponential, the following trigonometric series identities can be recognized:

$$\Phi(\kappa, \tau, \ell) = G(\kappa, \tau) \begin{bmatrix} \cos(\theta\ell) & \sin(\theta\ell) & 0 & 0 \\ -\sin(\theta\ell) & \cos(\theta\ell) & 0 & 0 \\ 0 & 0 & 1 & 0 \\ \frac{\kappa}{\theta^2}\sin(\theta\ell) & \frac{\kappa}{\theta^2}(1-\cos(\theta\ell)) & \frac{\tau\vartheta}{\theta} & 1 \end{bmatrix} G^T(\kappa, \tau)$$

Where $\Phi$ is a transformation from the state space to the catheter frame of reference. For the full $\Phi$ matrix, it is useful to leave the Given's rotations in the solution. However, the last row, which contains the Cartesian coordinate for a given arc length along the curve, is evaluated for each electrode on the hoop:

$$P(\kappa, \tau, \ell) = \begin{bmatrix} \frac{\kappa^2}{\theta}\sin(\theta\ell) + \tau^2\ell & \kappa(1-\cos(\theta\ell)) & -\frac{\kappa\tau}{\theta}\sin(\theta\ell) + \kappa\tau\ell & \theta^2 \end{bmatrix} \frac{1}{\theta^2}$$

Where P is a coordinate at position $\ell$ of the Frenet Fame. The model electrodes and/or coil(s) are then identified in the catheter reference frame by computing the arc length along a specified curve for each electrode, computing P as above and composing it with any $\Phi$ which may be more proximal.

For the model electrodes on the distal hoop (e.g., subscript 2 in the current embodiment) for the model of FIG. 6:

$$C_i = P\left(\kappa_2, \tau_2, \lambda_2 - \sum_{i'=1}^{i-1} \Delta_{i'}\right) \Phi_h \Phi_1(\lambda_1)$$

Where:

$C_i$ is the position of each electrode in the catheter frame of reference;

$\lambda_2$ is the length of the distal hoop curve;

$\Delta_{i'}$ is the intra-electrode distance specification (e.g., center to center);

$\Phi_h$ is a transformation between the curves of the first and second Frenet Frames to provide smoothing, and which in an embodiment where the first and second frames have a 90 degree clockwise rotation is:

$$\Phi_h = \begin{bmatrix} 1 & 0 & 0 & 0 \\ 0 & 0 & 1 & 0 \\ 0 & -1 & 0 & 0 \\ 0 & 0 & 0 & 1 \end{bmatrix}$$

$\Phi_1$ is the transformation for the distal hoop curve; and $\lambda_1$ is the length of the proximal shaft curve.

For the magnetic sensor or electrode (if present) on the proximal shaft of the two segment catheter model of FIG. 6:

$$C_i = \left[ \sum_{i'=1}^{2} \lambda_{i'} - \sum_{i'=1}^{i-1} \Delta_{i'} \quad 0 \quad 0 \quad 1 \right]$$

Once the positions of the model electrodes and/or magnetic sensors are known in the catheter reference frame, they may be transformed into the patient reference frame using any appropriate transformation. In an embodiment, six degree of freedom rigid transformation is utilized to orient the catheter model locations of the electrodes and magnetic sensor into the patient reference frame based on the position and orientation of the magnetic sensor relative to a position and orientation of a magnetic patient reference sensor. For each model electrode position in the patient reference frame, impedance measurements may be predicted and impedance measurements may be obtained (e.g., observed) from the physical electrodes. The predicted measurements and observed measurements may be utilized to update the parameters of the catheter model to more closely approximate a physical configuration of the deformable catheter.

While previously discussing the modeling of a relatively simple single spline catheter, it will be appreciated that more complex catheters may be modeled based on a limited set of parameters. FIGS. 8A-8D illustrate a planar catheter 140 having a substantially rigid shaft 142 having one or more magnetic sensors 148 and one or more electrodes (not shown) and a flexible paddle 144, which includes sixteen electrodes $146_{1-16}$ (hereafter 146 unless specifically referenced) arranged in a square matrix. In an embodiment, the planar catheter 140 corresponds to the HD Grid Catheter commercially available from Abbott Laboratories of Lake Bluff, Ill., United States. In the illustrated embodiment, the flexible paddle 148 is defined by four shape metal wires, which each support four electrodes 146. In a non-deflected or relaxed state, the flexible paddle 144 is substantially planar in the XZ plane with an origin at the end of the rigid shaft. A reference axis x extends from the origin longitudinally, for example, in axial alignment with the rigid shaft. In an embodiment, the catheter 140 is modeled as a curving plane with two model segments (proximal and distal). In addition to curvature, the axis of the distal segment's curvature may be rotated to capture off-axis deformations and both segments may be rolled laterally. The three-dimensional locations of electrodes may then be determined by the two-dimensional location on the curved plane. Further, the locations of electrode and/or sensors may be defined along the length of the various planes.

In an embodiment, the planar catheter is modeled by four parameters, a base curvature, a paddle curvature, a slanting angle and a tube curvature. Such parameters relate to physical actions that may occur during the course of a clinical procedure that would cause the catheter 140 to take a particular shape (e.g., deform). For instance, during a cardiac procedure the catheter 140 typically presses against a cardiac wall and/or is pushed into a lumen (e.g., blood vessel, artery). Pressing against a cardiac wall typically results in a change in the base curvature and paddle curvature from the relaxed state where the paddle 144 is displaced from the reference axis x as shown in the side view of FIG. 8B. Additionally, pressing against the sidewall may result in a slanting of the paddle 144 relative to the reference axis x as shown in FIG. 8C. Finally, displacing the catheter in a lumen may result in a cylindrical curvature along the length of the paddle 144 as shown in FIG. 8D.

Figure 8B:
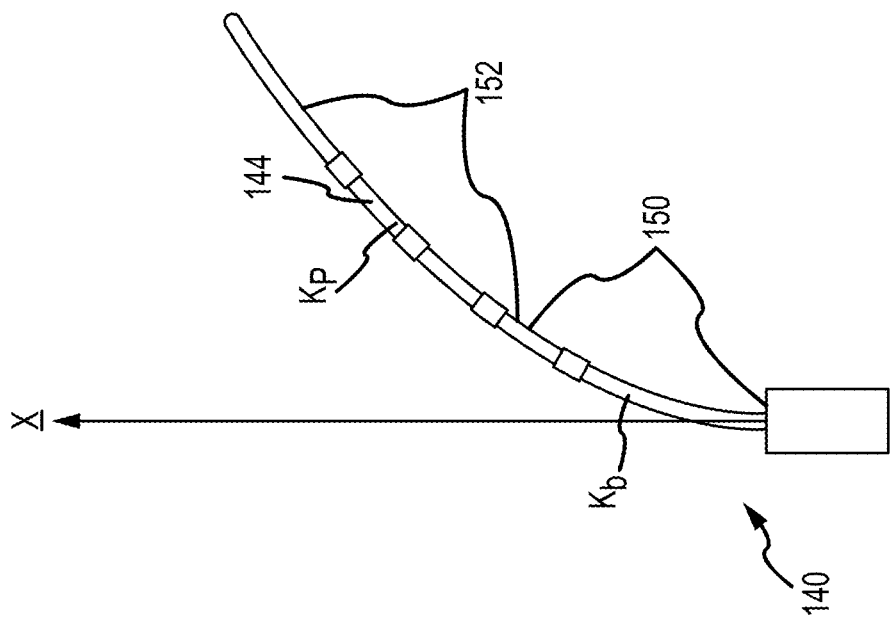
FIGS. 8A-8D illustrate various views of a catheter shape model of a planar catheter.
Figure 8A:
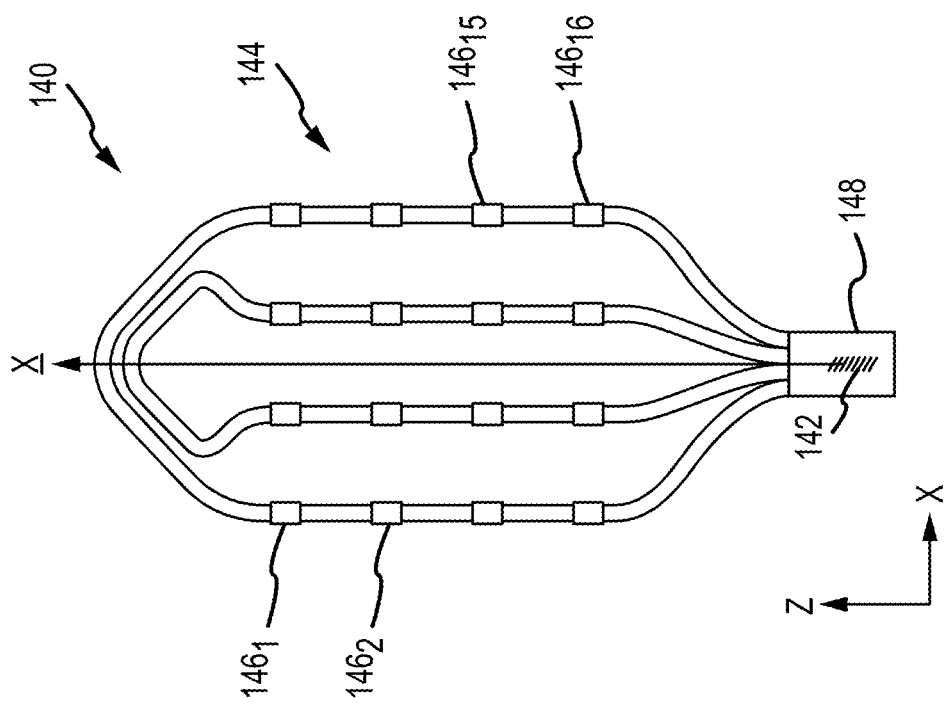
Figure 8D:
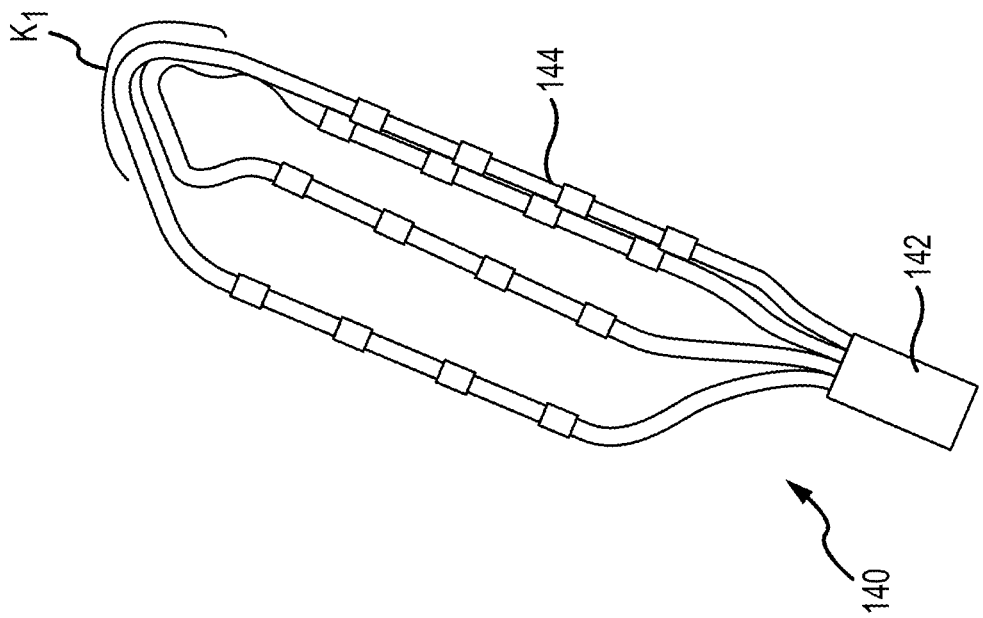
Figure 8C:
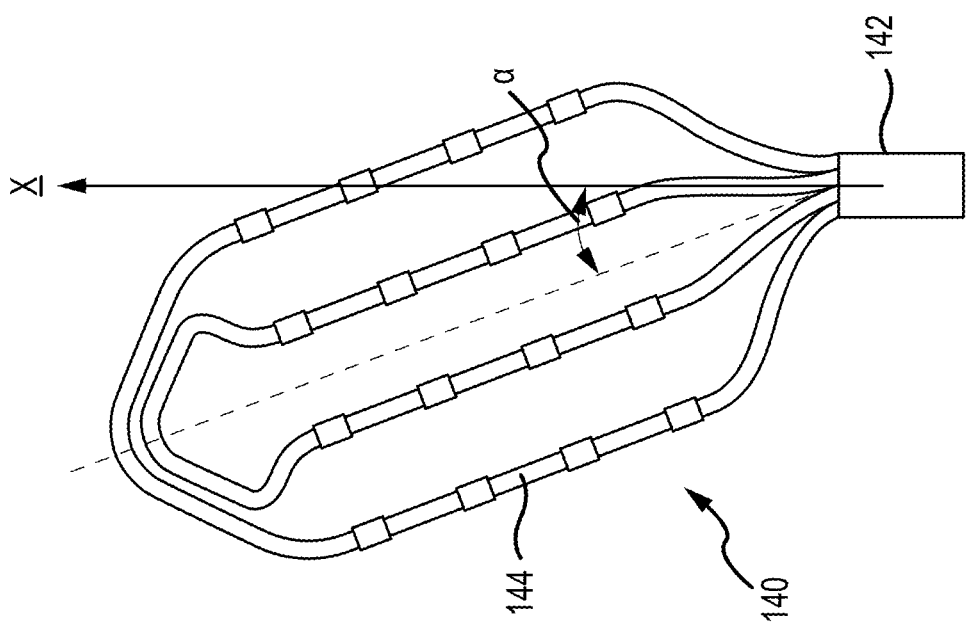

The base curvature $\kappa_b$ and paddle curvature $\kappa_p$ are best shown in FIG. 8B. As shown, the base curvature $\kappa_b$ corresponds to the curvature (e.g., inverse of radius) of the proximal segment 150 of the paddle 144 while the paddle curvature $\kappa_p$ corresponds to the curvature (e.g., inverse or radius $R_1$) of the distal segment 152 of the paddle 144. Through experimentation, it has been determined that, for the corresponding physical catheter, upright pressure on the paddle 144 (e.g., applied to the distal tip without slanting) results in the proximal segment 150 curving in a consistent manner. Accordingly, the base curvature $\kappa_b$ may be expressed by a single curvature parameter having a value range (e.g., ±0.25) that may be established based on expected curvatures or determined through experimentation. Typically, the proximal segment 150 of the paddle 144 is less rigid than the distal segment 152 of the paddle upon application of the same pressure. However, the curvature of the two segments are related. In an embodiment, the relationship between paddle curvature $\kappa_p$ and base curvature $\kappa_b$ can be expressed as:

$$\kappa_p \approx c \cdot f(\kappa_b)$$

where the functional factor f ($\kappa_b$) is positive. This relationship may be determined through experimentation where a number of paddle deformations are examined (e.g., in benchtop testing) to determine the shape or range of the base curvature. In an embodiment, a plot of the relative values of base curvature $\kappa_b$ and paddle curvature $\kappa_p$ may be prepared such that, for example, a best fit curve may define the relationship of the parameters. In an embodiment, the relationship between these curvatures for the specific catheter was found to be:

$$\kappa_p \approx c \cdot f(\kappa_b) = c \cdot c_1 \arctan(c_2 \kappa_b)$$

where c1 and c2 are experimentally determined constants.

FIG. 8C illustrates a slanting angle applied to the paddle. When upright pressing is exerted on a device, it can be imagined as wrapping around a generalized cylinder with lateral axis (i.e. perpendicular to the rigid shaft direction). A slanted pressing also results. in a generalized cylindrical surface, but its axis is not lateral, but rather has some angle α. The slanting angle may have an established range (e.g, ±45°). FIG. 8D illustrates the curvature or tube curvature $\kappa_t$ along the length of the paddle. By way of example, when the catheter is pushed into a lumen, the paddle attains a tubal shape, with curvature that is generally transverse to the longitudinal axis or reference axis x of the catheter. The catheter model utilizes the four noted parameters to define all possible shapes (e.g., states) that the planar catheter 140 may assume. Again, these parameters may define state variables in a stochastic process that predicts potential shapes of the model. Accordingly, based on the known spacing of the electrodes, their position may be determined for a possible state in the catheter reference frame in a manner similar to that described above.

The catheter models may be implemented to estimate shapes or states of a catheter as part of a stochastic process. In such an arrangement, a catheter model may be used to predict or estimate a current shape of a catheter and thereby the locations of electrodes in a catheter reference frame based on a previous known shape of the catheter. In such an arrangement, a shaping function may be applied to adjust each set of model parameters (e.g., previous curvatures, torsions, slant angles etc.) to estimate new potential catheter shapes. In such an arrangement, the model parameters may form hidden state variables and, in an embodiment, an Extended Kalman filter or other estimator may be used to estimate these hidden state variables to predict catheter shapes. In such an arrangement, a state distribution of all possible catheter shapes may be generated and transformed from the catheter reference frame to the patient reference frame to predict electrode locations within the patient reference frame. Predicted electrode measurements (e.g., from an impedance model) associated with the predicted locations of the electrodes in the patient reference frame (e.g., from the catheter model) may be utilized with actual electrode measurements in the patient reference frame to update a set of shape parameters associated with the updated shape estimate. This may allow identifying a true catheter shape and electrode locations in the patient reference frame.

When estimating or predicting the shape of a catheter described by a small number of parameters, it has been recognized that the shape estimation is over-determined. That is, the state distribution of predicted catheter shapes based on the shape parameters may include shapes that, while possible, are not likely. For instance, the loop catheter of FIG. 6 may be straightened by setting all curvatures to zero or the planar catheter of FIGS. 8A-8D may be rolled into a tight loop by when tube curvatures are set to large values. Neither condition is likely. Further, the electrode measurements all contain some error such that there is no combination of shape parameters that exactly reproduces the predicted or observed electrode measurements. Accordingly, it would be beneficial to eliminate unlikely states from the estimate to improve overall accuracy of the process.

In an embodiment, the present disclosure describes a technique for pruning the parameter space to physically achievable states by determining the likelihood of a set of shape parameters. More specifically, a likelihood function is applied to an estimated state distribution of the catheter shape model to exclude unlikely states from the estimated state distribution. This results in biasing the estimator towards more likely parameters.

In an embodiment, the likelihood function may be determined experimentally by deforming a physical catheter associated with a catheter model under constant force and computing the energy associated with a set of shape parameters for each shape of the catheter. The stored energy may then be used as proportional to the negative log likelihood of an associated set of shape parameters for particular catheter shape. Along these lines, it is recognized that many catheters have one or more shape memory wires or splines that, when deformed, attempt to return to a nominal or original configuration. By way of example, the planar catheter discussed above may return to the planar configuration once a deforming force is removed from the catheter. Accordingly, the energy stored in the catheter when bent may be assumed to be proportional to the likelihood of the deformation. When a catheter is deformed by pushing it against a structure, it may be assumed that the catheter will adopt the lowest-energy configuration. For example, for a deformation in response to an obstacle, if a lower energy configuration can produce the same measurements, the catheter will be in the lower energy configuration. Thus, it follows that the energy of a deformation is proportional to the likelihood of the corresponding set of shape parameters.

FIG. 9 illustrates a testing system 200 for experimentally determining the energy of deformation of a catheter 140 in a bending procedure. As shown, the system has support or collet 202 that receives and holds the shaft 142 of the catheter 140 in a known orientation, a movable sled 210 and actuator 212 that displaces a distal end of the catheter, a force sensor 220, one or more cameras 230 and a controller 232. The system is utilized to apply deformations of known magnitude and/or displacements and record the locations of the catheter electrodes 146 in 3D space.

The collet 202 holds the catheter shaft at a desired roll angle α. In an embodiment, the collet is configured to rotate about an axis that is substantially co-axial with the longitudinal axis of the catheter shaft. Thus, the collet may rotate to any desired roll angle α. During each bending procedure, the catheter shaft may be maintained at a predetermined fixed roll angle. The movable sled 210 is moved into contact with the distal end of the catheter at an angle theta Θ (e.g., contact angle) to the longitudinal axis of the catheter 140. The sled 210 is attached to an actuator 212 through the force sensor 220. The sled 210 is then controllably displaced by the actuator 212 which is configured to maintain a force set point (e.g., via PID control). The sled 210 is displaced toward the catheter until it contacts the distal end of the catheter at a known angle theta Θ and the force set point is achieved. Once an initial force set point is achieved, the sled may be additionally displaced for additional force set points. For each advancement or displacement of the sled and force set point, the catheter is bent or deformed. By recording the displacements and the forces, these may be integrated to compute the energy stored in the catheter. Similar processes may be provided where the distal end of the catheter is displaced (e.g., pushed) into a lumen of a known size and orientation.

Figure 10:
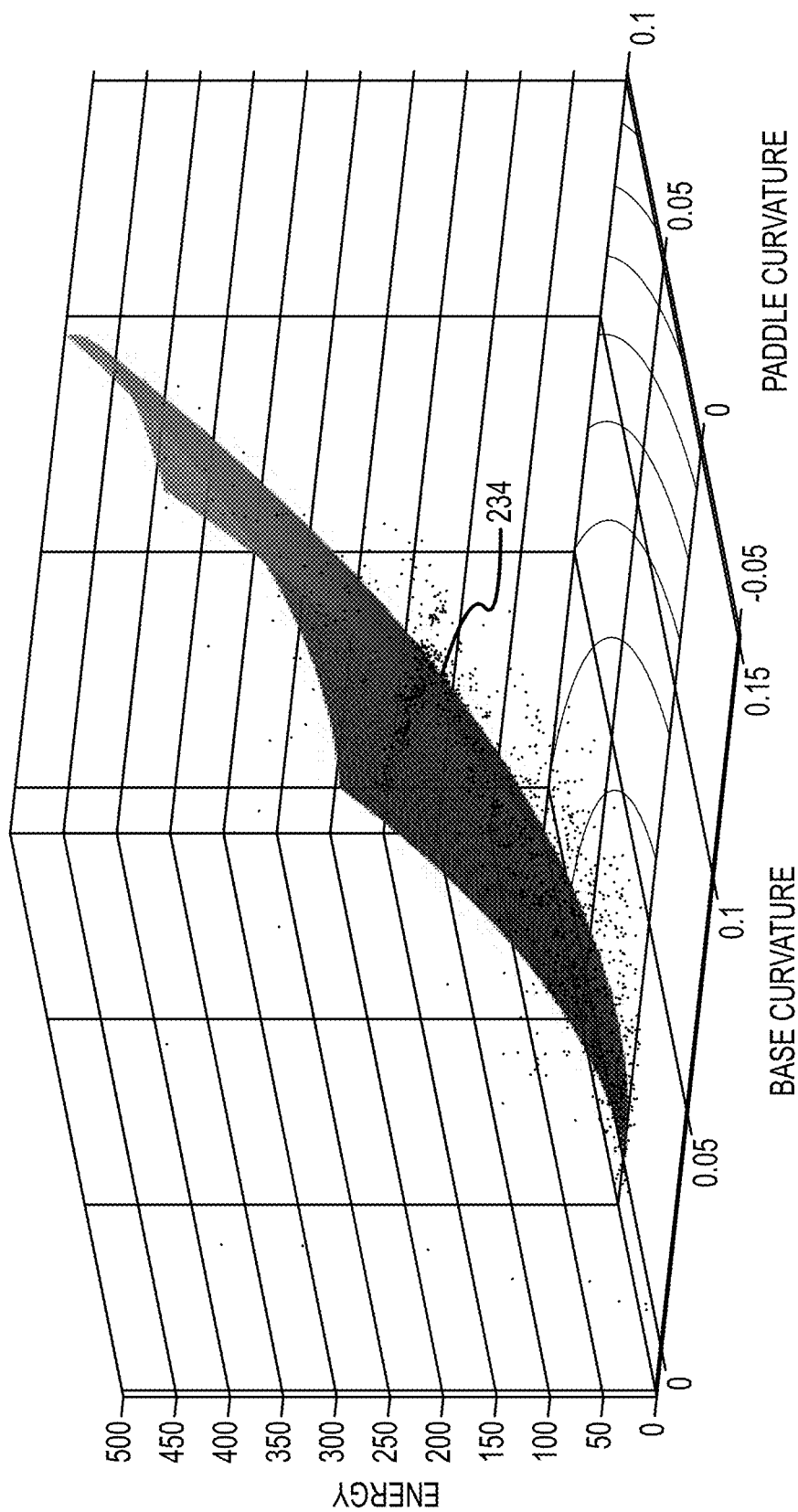
FIG. 10 illustrates curvatures of proximal distal segments of a planar catheter.

This bending procedure is conducted in a calibrated multicamera system. That is, cameras 230 identify the position of each electrode 146 such that a low-error 3D coordinate of each electrode is determined for each deformation. The controller 232, for each deformation, utilizes the coordinates from the cameras, the angular information from the collet and sled, the forces and the displacements to determine corresponding shape parameters (e.g., curvatures, slanting angles etc.). In an embodiment, a nonlinear least-squares minimization of the shape, position and orientation parameters is used to find the shape parameters associated with a particular deformation. By iterating the constant force displacement over the permutations of alpha, theta and force, samples of the shape/energy landscape are acquired. Curves describing the energy as a function of the shape parameters can then be fit to the samples. FIG. 10 shows an example over the curvatures of the proximal and distal plane segments of the catheter 140. Numerous curves may be generated for any given catheter.

In an embodiment, the experimentally determined curves are the basis of the likelihood function r(x). The likelihood function is used to regularize an estimated state distribution. Generally, the likelihood function describes the plausibility of a state (e.g., catheter shape). In an embodiment, a negative log likelihood is utilized. In such an embodiment, impossible states have a negative log likelihood of infinity and the most likely state has the minimum negative log likelihood. To apply this regularization, in an embodiment, a probability density function (regularizing PDF) is computed by negating, exponentiating and normalizing the negative log function. The estimated state distribution is then multiplied by the regularizing PDF and renormalized to create a regularized state distribution that omits unlikely states (i.e., states outside the combination of the state distribution and the regularizing PDF).

In an embodiment, the log likelihood function may be approximately applied through a second-order Taylor series expansion of the negative log likelihood function at the mean of the estimated state distribution to create a probability density function. In an embodiment, the approximation of the negative log likelihood function may be made via the following equation:

$$-\ln r(x) \approx -\ln r(x') - \mathcal{L}(x-x') - \frac{1}{2}(x-x')^T \mathcal{H}(x-x')$$

Where the Hessian $\mathcal{H}$ of the second order expansion is treated as the inverse of the covariance, with the Gaussian mean given by the multiplication of the Jacobian of the second-order expansion by the inverse of the Hessian. This approximation is equivalent to a Guassian PDF, which can be multiplied with the state distribution by well understood means.

Figure 7B:
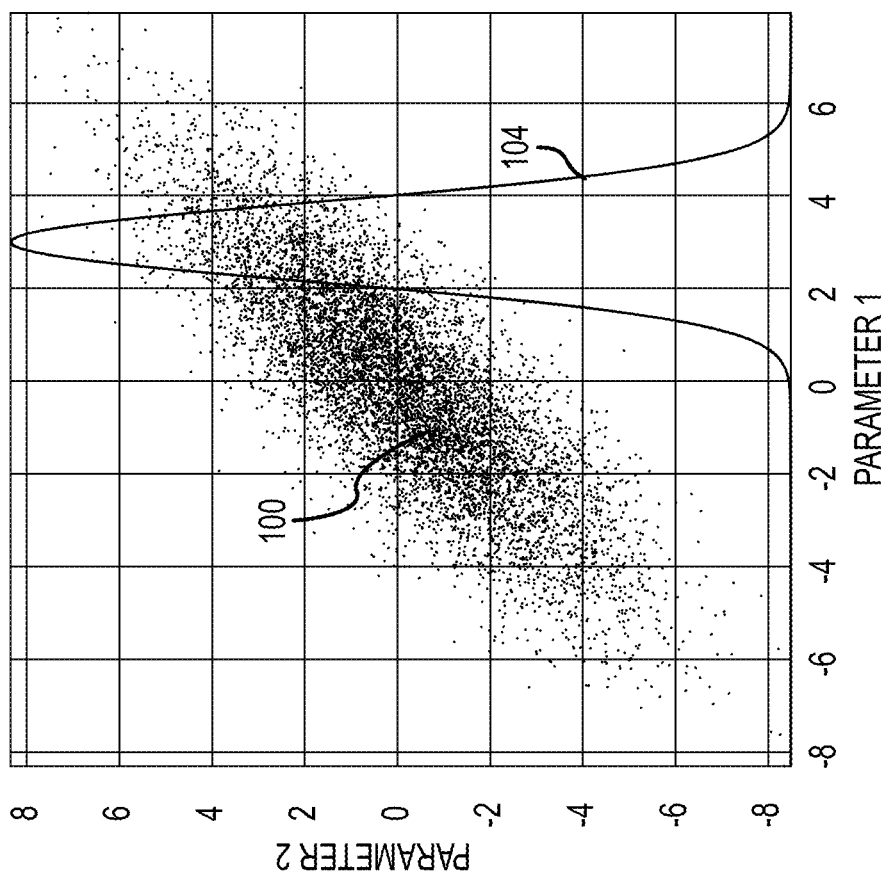
Figure 7C:
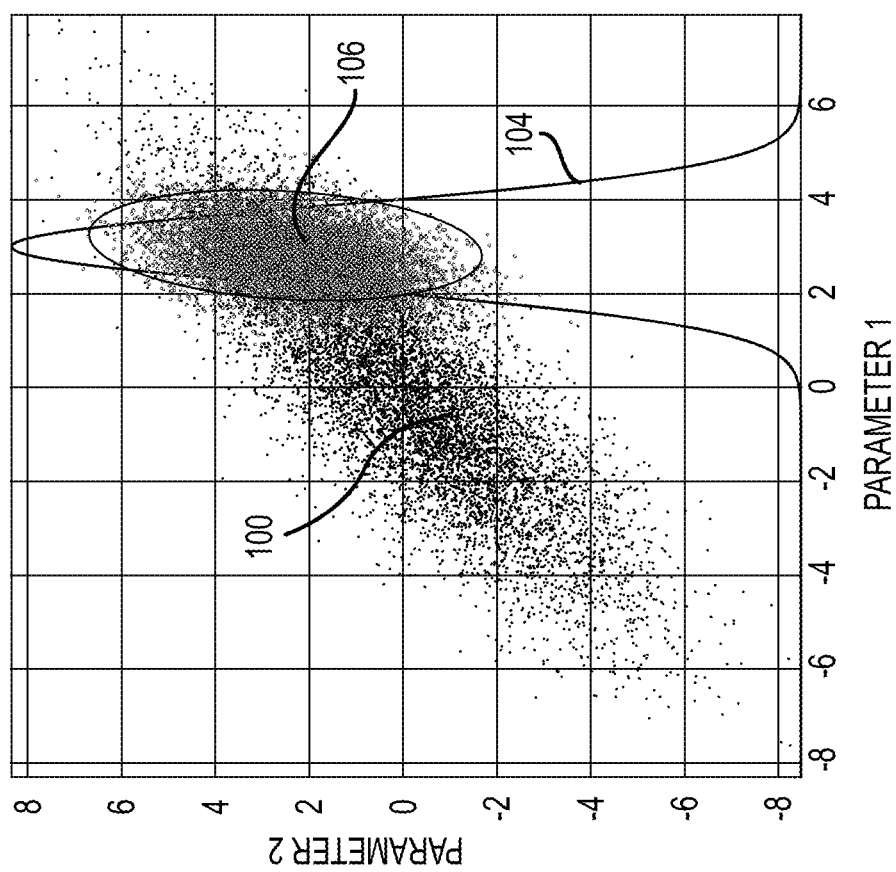

The regularization of a state distribution estimate is graphically illustrated in FIGS. 7A-7C. Specifically, FIG. 7A shows the state distribution 100 of possible catheters shapes predicted by a catheter model. FIG. 7B shows the regularization PDF 104 applied to the state distribution. FIG. 7C illustrates the regularized state distribution 106, which is generally enclosed by a dashed circle for purposes of illustration. As will be appreciated, the regularized state distribution excludes unlikely states from the initial state distribution estimate. This results in a new or updates state distribution (e.g., regularized state distribution) having an updated mean and an updated covariance. Stated otherwise, the regularization process results in a tighter state distribution that more accurately predicts the true state of the system.

Catheter Position and Orientation Model

For any catheter model having a magnetic sensor, the magnetic sensor will typically define a vector having six degrees-of-freedom. Three degrees-of-freedom for position (i.e., x, y, z), which may define an origin model in the catheter reference frame as defined by one or more magnetic sensors of the model, and three degrees of freedom for orientation (i.e., yaw, pitch, roll). The three degrees of freedom for the orientation may define a 3D bivector ($b_{yz}$, $b_{zx}$ and $b_{xy}$), which is the log of the quaternion. The catheter shape model may be transformed into the patient reference frame utilizing a transformation (e.g., catheter transformation) that preserves shape and size of the catheter model. That is, catheter position and orientation model may be represented by a rigid-body transformation (e.g. six degree of freedom rigid-body translation) that translates the vector (e.g., state vector) of the shape model into the patent reference frame. For instance, such a transformation may align the origin and orientation of the catheter model (e.g., vector in an embodiment) relative to the origin of the patient reference frame (e.g., as determined by the patient reference sensor). At such time, the locations of the magnetic sensor and electrodes are known or estimated within the patient reference frame. Of note, the origin of the patient reference frame as well as the origin of the catheter reference frame may shift due to patient motions (e.g., respiration, physical patient movement, etc.). Accordingly, the transformation and registration between the patent reference frame and the catheter reference frame may be updated.

Magnetic Model

The following provides one magnetic model that transforms from patient relative coordinates (e.g., patient reference frame) to the magnetic-based coordinate system. That is, the magnetic model takes a location in the patient reference frame having an origin defined by the PRS and generates a location in the magnetic reference frame. In an embodiment, the magnetic model is a rigid transformation from the patient coordinate frame/patient reference frame to the magnetic-based coordinate system. As noted, the origin of magnetic based coordinate system is based on the magnetic-field generator while the origin of the patient reference frame is defined by the patient reference sensor. In an embodiment, the origin of the patient reference frame may be offset from the patient reference sensor. In such an embodiment, a coordinate may be mapped through the following relationships as if they were 4×4 matrices in homogenous coordinate systems:

$$pat_k = PRSToPat_k ref_k$$

$$mag_k = PatToMag_k pat_k$$

where $ref_k$ is the value of a coordinate in the patient space at time k, $pat_k$ is the value of the coordinate aligned with the patient reference frame at time k, and $mag_k$ is the value of the coordinate in magnetic-based coordinate system at time k. The PRSToPat transformation rotates the coordinate to the patient frame of reference while the PatToMag transformation rotates the coordinate to the magnetic frame of reference. In an embodiment, these relations may be used to generate a magnetic value for a location in the patient reference frame. It will be appreciated that additional magnetic models are possible and considered within the scope of the present disclosure. In an example, a magnetic model for use in transforming between patient relative coordinates to magnetic coordinates is described in the application titled "Patient Reference Sensor Model for Medical Device Localization based on Magnetic and Impedance Sensor Measurements", filed on Nov. 7, 2018, the entire contents of which is incorporated by reference.

The magnetic model may form a part of the overall or composite system model. During implementation, the model is queried to predict sensor locations in the patient reference frame. Subsequently, these predictions are utilized with sensor locations measurements to further refine the estimated locations of the sensors in the patient reference frame.

Impedance Model

Within the context of a sensor fusion process, the usefulness of impedance measurements to locate catheters depends on having an effective model, for any catheter configuration, to predict the impedance measurements within an electrical or impedance potential field, which correspond to locations of the catheter electrodes in the potential field. That is, based on an estimated location of a catheter electrodes in a patient reference frame, it is desirable to predict the impedance measurements of the catheter electrodes for that location for comparison with an actual electrode measurement to refine the location of the catheter and/or its electrode(s). It has been further recognized that previous efforts of impedance modeling of electrodes locations has, in some instances, lacked accuracy due to the failure to account for noise.

In an embodiment, an impedance model is provided that transforms between the patient coordinate system and the impedance measurements (e.g., PatToImp). Generally, the model is defined as a stochastic process where a true state of the model, which is a hidden or latent state, is determined. The model generates estimates of the electrode impedance measurements in space (e.g., location-to-impedance-value). Such estimates may be refined based on actual measurements of the electrode impedances to determine true impedance measurements for the electrodes. In an embodiment, modeling the location-to-impedance-value is performed as a mapping as a linear combination of harmonic basis functions, such as the regular solid harmonics.

The hardware for impedance-based location measurements consists of a set of electrical patches affixed to the patient (e.g. 6 patches: neck, leg, chest, back, right, left). AC voltages are applied to sets of patch pairs (e.g. back→left, left→chest, right→back, chest→right, neck→back, leg→back) and the potentials (e.g., impedances) on each catheter electrode are measured while each patch pair is driven. The potential measured depends on the relative impedances between the electrode and each of the driven patches. That is, each driven patch pair induces a potential field across the patient that the electrodes measure. Accordingly, the intent of the impedance model is to model the potential field and its measurement characteristics such that an impedance measurement may be estimated for any location within the potential field. By way of example, once the locations of electrode in a patient reference frame are known or estimated for a given time (e.g., based on a catheter model), impedance measurements (e.g., estimates) may be generated for those locations at this given time. Such estimates may then be refined based on comparisons with actual measurements.

Each time point and for each independent driven patch pair or 'impedance mod', model impedance measurements for each independent potential field i and electrode j are set forth as follows:

$$y_{ij} = \varphi_{ij} + \varepsilon_{ij}$$

and:

$$z_k = Vec(My_j) + v_k$$

Where $\varphi_{ij}$ is a potential in independent potential field i for electrode j computed from a series of harmonic bases $Y_\ell$, $\varepsilon_{ij}$ is a modeling error term which covaries between a pair of electrodes as function of their distance, and $\omega_i$ is a measurement noise term.

For each independent driven patch pair or impedance mod i', $\varphi_{i'j}$ is a function of the electrode location $x_j$ (e.g., in the patient reference frame) and of the state variables of the impedance model (e.g., Patient to Impedance transformation). In an embodiment, the impedance transformation may be a global dynamic non-rigid transformation that maps the patient frame of reference to the impedance frame of reference. $\varepsilon_{i'}$ is the vector of all distance dependent modeling error terms for impedance mod i' and is modeled as a multivariate normal random variable whose entries have a covariance dependent on the distances between pairs of electrodes. Finally, $\omega$, the vector of the electrical noise terms for all electrodes, is a multivariate normal random variable reflecting electrical noise characteristics of the measurement system. This model of impedance measurement behavior is used as part of the sensor fusion process or algorithm, such as a recursive Bayesian estimator (e.g. an extended Kalman filter or particle filter), to fit impedance and catheter state variables to the impedance and other measurements.

In an embodiment, $\varphi_{ij}$ is a linear combination of basis functions. Each basis function at a point in space maps to an electrical value of the modeled potential field to an electrical value (e.g., voltage, impedance, etc.). Each basis function at a point in space maps to an electrical value of the modeled potential field to an electrical value (e.g., voltage, impedance, etc.). If electrodes are at locations $x_j$ then:

$$\varphi_{ij} = \sum_\ell b_{i,\ell} Y_\ell(x_j)$$

Where $Y_\ell$ is a scalar-valued function evaluating the $\ell$ th solid harmonic basis function for an electrode location, and $b_{i,\ell}$ is the weights on the basis functions (e.g., $\ell$ th basis function) relating the patient frame of reference to the impedance potential field. All basis functions $g_k$ should be harmonic. That is, the Laplacian everywhere should be zero. In an embodiment, $g_k$ can be the regular solid harmonics of up to a predetermined order. For example, $Y_\ell$ can be the regular solid harmonics of up to the fourth order. Use of harmonics up to the fourth order results in 25 basis functions per electrode. As will be appreciated, limiting the harmonic basis functions to the fourth order truncates information in higher order harmonics, which may provide additional description of the potential field. The exclusion of this information is accounted for in the modeling error term ε. In an embodiment, the modeling error include a respiration induced artifact. In an example, a system and method for modeling a respiratory error or artifact is described in the application titled "Respiration Model for Device Localization Based on Impedance Sensor Measurements", filed on Nov. 7, 2018, the entire contents of which is incorporated herein by reference.

In an embodiment, an Extended Kalman filter is used to infer hidden state variables corresponding to the hidden state variables of the model. From the hidden state variables, at any time, hidden state measurements (e.g., impedance values at locations in space) can be predicted and estimates of the state variables can be updated using an Extended Kalman filter framework in a fashion that allows updates to those parts of the hidden state variables that are accessible. Thus, at any instant in time, while there may not be enough information to determine parts of state variables, by using the Extended Kalman filter framework, predictions associated with appropriate parts of the state variables associated with the transformation from the location in the patient reference frame to impedance measurement can be made.

The impedance model forms a part of the overall or composite system model. During implementation, the impedance model is queried for use with predicted electrode locations in the patient reference frame as estimated by the catheter model. More specifically, the impedance model is used to predict measurements for each electrode location in the patient reference frame. Subsequently, these predictions are utilized with actual electrode measurements to further refine the estimated locations of the electrodes in the patient reference frame as well as update the impedance model. In an example, impedance models for use in determining impedance measurement or values for a location in a patient reference frame are described in the application titled "Impedance Transformation Model for Estimating Catheter Locations", filed on Nov. 7, 2018, the entire contents of which is incorporated herein by reference.

Collectively, the models fully describe the movement of the medical device. Stated otherwise, the models describe possible states of a stochastic process and represent individual state variables of the system. Generally, knowledge of the state variables at an initial time with at least partial knowledge of system inputs and/or outputs permits estimating current states and/or subsequent states of the system as points or a distribution in a state space. The state of the system can be represented as a distribution 100 of possible states within the state space (i.e., represented as points in the state space). See, e.g., FIG. 7A.

The overall system is a stochastic process as are a number of the system components (e.g., individual models). To provide improved modeling and estimation of the system, noise should be included within the system model. The observational model utilizes new measurements (e.g., with some amount of noise) with the previous state of the system to estimate a new state of the system. In an embodiment, the process fuses impedance measurements from electrodes of a physical catheter with predicted electrode measurements based on a catheter model to update the predicted shape of a medical device or catheter disposed within a patient reference frame. The disclosed system may predict and update states of the system approximately 100 times per second. For instance, the variable shape parameters and catheter shape predicted by the catheter model may be updated 100 times per second. Accordingly, the system provides near continuous updates of predicted states of the system.

The overall stochastic process estimates new locations of the medical device and/or new locations of the electrodes of the medical device. In an embodiment, the process assumes that the state of a system at time k evolved from a prior state at k−1 according to the equation:

$$x_k = F_k(x_{k-1}) + w_k$$

where:

$x_k$ is the state vector containing parameters of interest for the system (e.g., parameters of the models). This equation is used to predict subsequent states with error.

$F_k$ is the state transition matrix which applies the effect of each system state parameter at time k−1 to the system state at time k.

$w_k$ is the vector containing process noise terms for each parameter (e.g., model) in the state vector.

Measurements of the system, with error, are also performed at each time step according to the model:

$$z_k = h_k(x_k) + v_k$$

where:

$z_k$ is the measurement vector; the set of variables measured by the sensors (e.g., impedance measurements, magnetic sensor measurements, etc.).

$h_k$ is the observational model (i.e., transformation matrix) that maps the state vector parameters into the measurement domain. Stated otherwise, the observational model defines the relationship between the true state vector and noisy measurements; and $v_k$ is the vector containing the measurement noise terms for each measured variable in the measurement vector.

The stochastic process is utilized to determine a true state of the system and or system models, which are hidden or latent states. The purpose of the process it to generate estimates of the system state (e.g., electrode locations, hidden variables of the models) and determine the true state from these estimates. In an embodiment, an estimator is implemented in an extended Kalman filter adapted for use with non-linear system models or linearized system models and/or with models having non-Guassian noise distributions. However, it will be appreciated that variations may be implemented using other estimators such as the unscented Kalman filter, Markov Models and/or particle filters, which each may be applied to nonlinear systems and/or systems with non-Gaussian noise distributions.

Each estimate of the estimator is a mean (i.e., center of a distribution of state estimates) and covariance describing a probability about the mean. In application, the estimates include an a priori estimate (predict) prior to incorporating the measurements and an a posteriori estimate (update) after incorporating the measurements. The a priori estimate uses the state estimate from the previous time step to produce an estimate (e.g., prediction) of the latent state (mean $\underline{x}_{k|k-1}$ and covariance $\underline{P}_{k|k-1}$) at the current time step:

$$\underline{x}_{k|k-1} = F_k \underline{x}_{k|k-1}$$

$$\underline{P}_{k|k-1} = F_k \underline{P}_{k|k-1} F_k^T + Q_k$$

That is, the a priori estimate is an estimate from the transformation matrix that produces an estimated distribution and covariance from the prior state (i.e., k−1). The transformation matrix takes every point in the original distribution and moves it to a new predicted distribution, which may have an expanded covariance (e.g., the addition of $Q_k$ to the covariance matrix P) to account for unknown system noise. In the a posteriori estimate, the current a priori prediction is combined with the observation model to refine the state estimate. More specifically, the observational model maps the estimation (e.g. mean $\underline{x}_{k|k-1}$ and covariance $\underline{P}_{k|k-1}$) to the measurement domain to predict measurements:

$$\underline{z}_k = h_k \underline{x}_{k|k-1}$$

The covariance of predicted measurements $\underline{z}_k$ may be compared with the covariance actual measurements $z_k$ of observable parameters (e.g., electrode measurements and sensors measurements of the system):

$$y_k = z_k - \underline{z}_k$$

Figure 11:
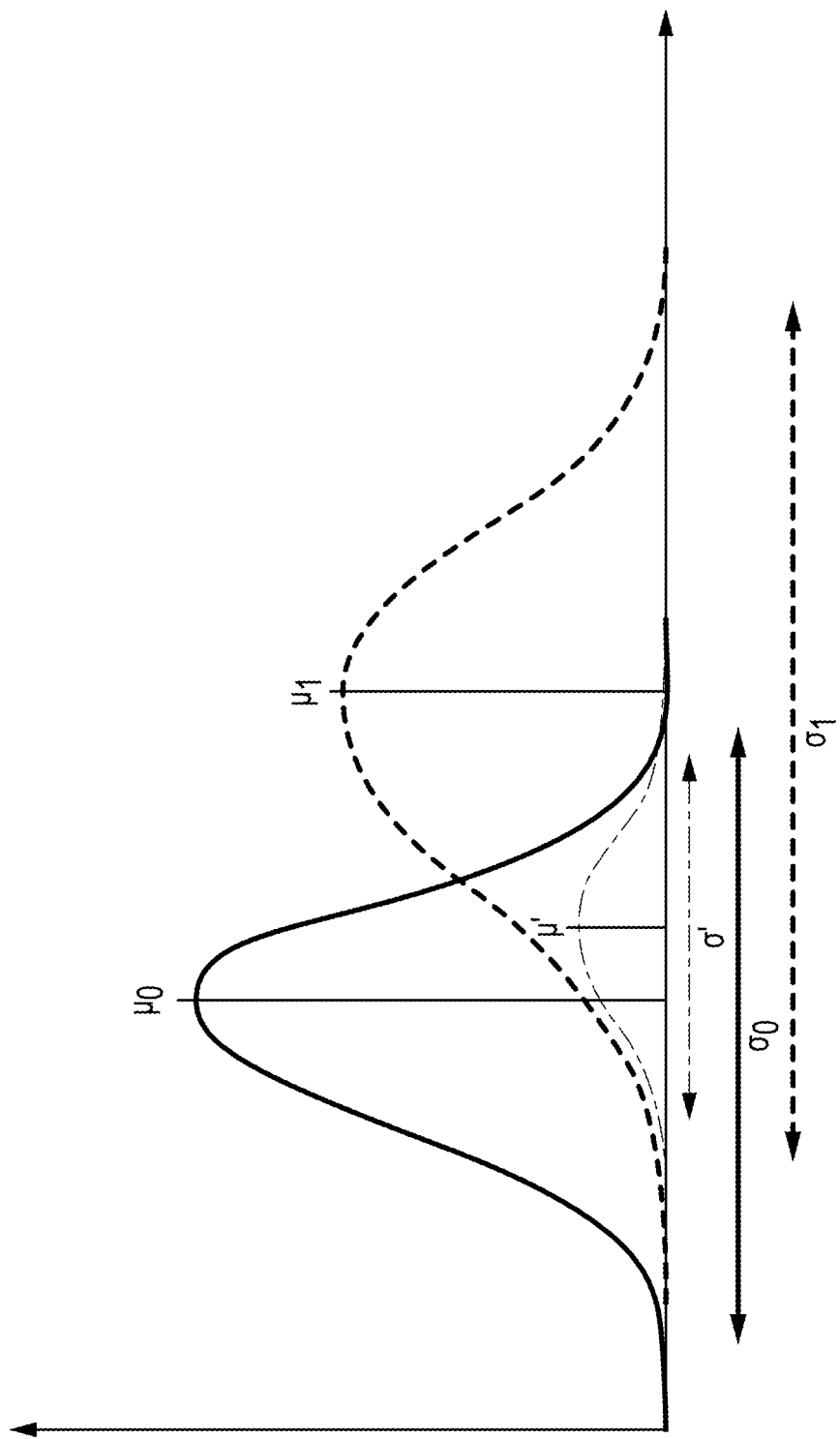
FIG. 11 illustrates one-dimensional comparisons of predicted and observed states.

This allows for determining the gain K of the system, where K minimizes the expected sum squared error between $\underline{x}_{k|k} - x_k$. This is graphically illustrated in FIG. 11 which is a 1-D representation of the state distribution combined with the observational model that produces the predicted measurements with a first predicted mean $\mu_o$ and a first predicted covariance $\sigma_o$. The actual observation measurement is represented by a second distribution with a second mean $\mu_1$ and a second covariance $\sigma_1$. The overlap of these distribution defines the system gain (e.g., Kalman gain), which is used to correct the estimated state and estimated covariance. Stated otherwise, the two distributions are fused to generate an updated distribution with a fused mean $\mu'$ and a fused covariance $\sigma'$ (e.g., two Gaussian distributions multiple together generate an Gaussian distribution of the overlapping portion of these two distributions). The overlap of these distributions defines the most likely set of potential states. The gain K may be combined with the estimated state distribution and estimated covariance to generate an updated state distribution (e.g., updated state mean and updated covariance):

$$\underline{x}_{k|k} = \underline{x}_{k|k-1} + K_k y_k$$

$$\underline{P}_{k|k} = (I - K_k H_k) \underline{P}_{k|k-1} (I - K_k H_k)^T + K_k R_k K^T.$$

The updated mean state may be utilized to determine updated or true locations (e.g., calculated locations) of the electrodes and/or magnetic sensors. Further, this state may be utilized to update the various state variables of the various models. In an example, multiple models for use in determining electrode and or sensor locations in three-dimensional space (e.g., a patient reference frame) are described in the application titled "Method for Medical Device Localization Based on Magnetic and Impedance Sensors", filed on Nov. 7, 2018, the entire contents of which is incorporated herein by reference.

Figure 12:
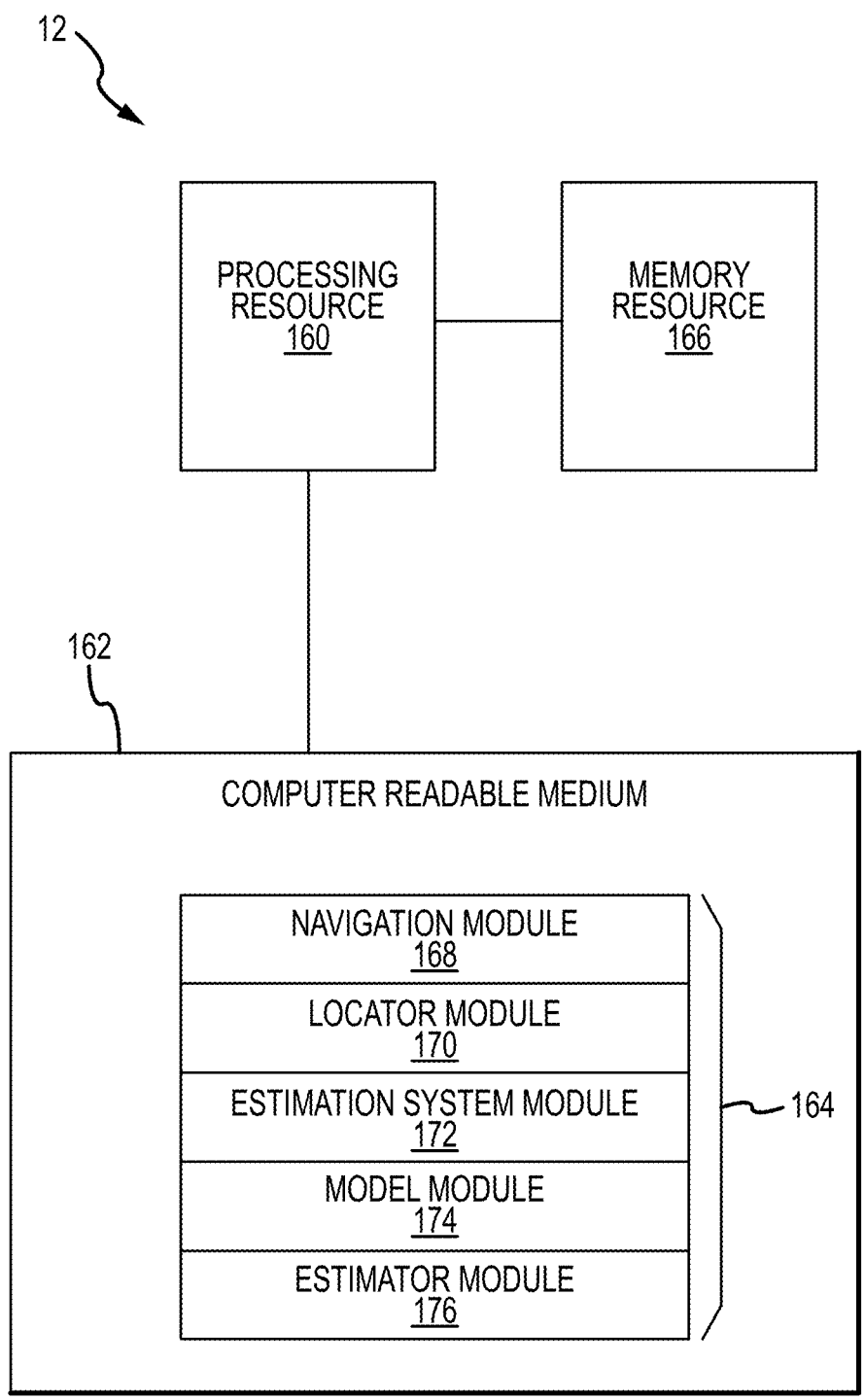
FIG. 12 illustrates a block diagram of an example of a computer-readable medium in communication with processing resources of a computing device, in accordance with embodiments of the present disclosure.

FIG. 12 depicts a block diagram of an example of a computer-readable medium in communication with processing resources of a computing device, in accordance with embodiments of the present disclosure. The main control 12, as discussed in relation to FIG. 1, can utilize software, hardware, firmware, and/or logic to perform a number of functions. The main control 12 can include a number of remote computing devices.

The main control 12 can be a combination of hardware and program instructions configured to perform a number of functions. The hardware, for example, can include one or more processing resources 160, computer readable medium (CRM) 162, etc. The program instructions (e.g., computer-readable instructions (CRI) 164) can include instructions stored on CRM 162 and executable by the processing resource 160 to implement a desired function (e.g., determine an updated location of an electrode on an impedance based medical device using the observation model, etc.). The CRI 164 can also be stored in remote memory managed by a server and represent an installation package that can be downloaded, installed, and executed. The main control 12 can include memory resources 166, and the processing resources 160 can be coupled to the memory resources 166.

Processing resources 160 can execute CRI 164 that can be stored on an internal or external non-transitory CRM 162. The processing resources 160 can execute CRI 164 to perform various functions, including the functions described above.

A number of modules 168, 170, 172, 174, 176 can be sub-modules or other modules. For example, the estimation module 172 and estimator module 174 can be sub-modules and/or contained within a single module. Furthermore, the number of modules 168, 170, 172, 174, 176 can comprise individual modules separate and distinct from one another.

A navigation module 168 can comprise CRI 164 and can be executed by the processing resource 160 to acquire measurements from a medical device 24 and/or render an output corresponding to the medical device on a display 16. The measurements can include impedance measurement of an electrode disposed on a physical catheter and/or impedance surface patch measurements. The measurements can also include magnetic locations of a magnetic position sensor disposed on the catheter and/or magnetic measurements of a patient reference sensor. The navigation module 168 may call the locator module 170 to obtain updated location predictions for electrodes and/or sensors of the medical device 24.

A locator module 170 can comprise CRI 164 and can be executed by the processing resource 160 to coordinate the operation of the estimation module 172, the model module 174 and the estimator module 176. In an example, the locator module can receive raw measurements form the navigator module in conjunction with an update request. The locator module 170 may call function of the estimation system module 172 to pre-process the raw measurements. Once the pre-processed measurements are acquired from the estimation module, the locator module 172 may provide the pre-processed measurements to the estimator 176 to with a request to update the current state of the system.

The estimation system module 172 can comprise CRI 164 and can be executed by the processing resource 160. In an embodiment, the estimation system module 172 defines the stochastic process of the overall system and individual models including the state transition(s) and the observational model(s). In an embodiment, the estimation system may be a Kalman system that that implements Kalman filtering techniques. In an embodiment, the estimation system module 172 calls the model module 174 to and estimator module 176 to obtain an updated state estimate.

A model module 174 can comprise CRI 164 and can be executed by the processing resource 160. The model module may include a plurality of individual models. These individual models may include one or more catheter models and their various shape parameters. In an embodiment, a single medical device/catheter may be represented one or more models. Additionally, catheter models may include models of different medical devices for use when more than one catheter is within a patient reference frame. The individual models may also include a magnetic model (e.g., magnetic transformation model) that transforms locations from the patient reference frame of reference to the magnetic reference frame. The individual models may also include an impedance model or impedance transformation model that predicts impedances for locations in the patient reference frame.

An estimator module 176 can comprise CRI 164 and can be executed by the processing resource 160. The estimator module may receive update requests and inputs from the estimation system 172 and provide updated state estimates and/or predicted measurement in response. In an embodiment, the estimator module may be implemented as an extended Kalman filter.

Figure 13:
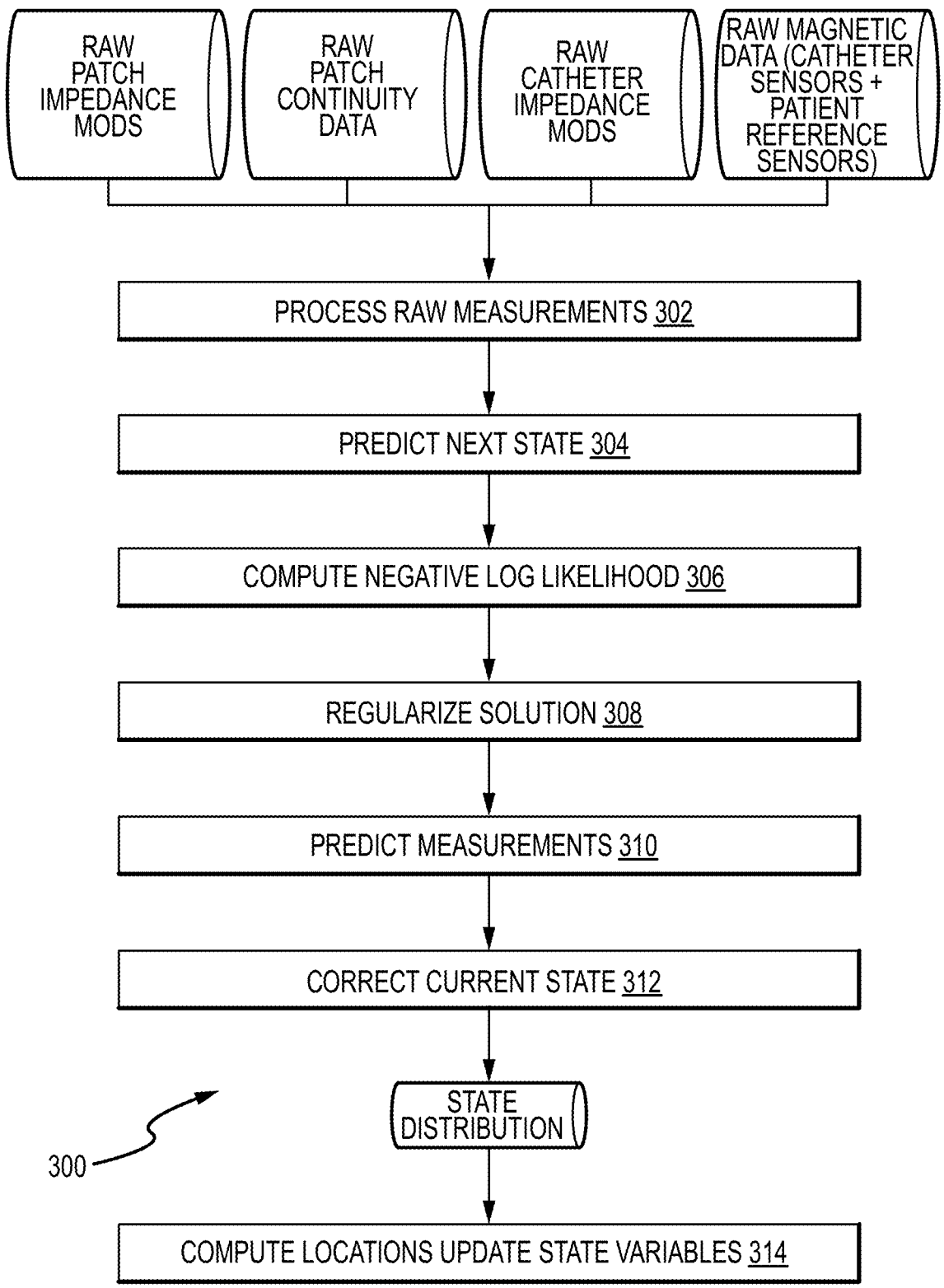
FIG. 13 illustrate a flow diagram associated with determining a latent state of a system to identify electrode locations, in accordance with embodiments of the present disclosure.

FIG. 13 depicts a flow diagram 300 associated with an overall process to update estimated electrode locations within the three-dimensional space, in accordance with embodiments of the present disclosure. Initially, the flow diagram includes processing raw measurements at box 302. Raw measurements may include raw patch impedance measurements from the surface patch electrodes as well as patch continuity data. The patch continuity data may provide an indication regarding the contact of each surface patch and, hence, reliability of the same. Raw electrode impedance measurements are also received for electrodes of the medical device/catheter (hereafter catheter). Raw magnetic data is also received for magnetic sensors of the catheter and for the patient reference sensor. Processing the raw measurements may include processing to raw measurements to detect any measurements that are outside a predetermined statistical range for the measurements (e.g., have a non-Gaussian error). Any such outlaying measurements may be excluded from subsequent processing.

The next state of the system is predicted at box 304 of the flow diagram. That is, a new distribution (e.g., mean and covariance) of the state is generated using the state transition matrix $F_k$ which applies the effect of each system state parameter at time k−1 to the system state at time k and the covariance matrix. In an embodiment, unlikely states in the current state are penalized to reduce the distribution of the current state. In an embodiment, a negative log likelihood is computed at box 306 of the flow diagram. In an embodiment, a probability density function is generated and applied to the current state distribution. That is, the current state distribution may be regularized at box 308 of the flow diagram.

Predicted measurements may be generated at box 310 of the flow diagram. That is, the observational model may be utilized to predict measurements (e.g., electrode and sensor location measurements) given the current predicted state to produce a distribution of predicted measurements having a mean and covariance. Once the measurements are predicted, they may be utilized with actual measurements to determine a correction that may be utilized to correct the current predicted state at box 312 of the flow diagram. At this point a new state distribution is generated for the current update (e.g., time step). From the state distribution, catheter shape and electrode locations may be computed at box 314 of the flow diagram. Additionally, the shape parameters (e.g., state variables) of the catheter model may be updated.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for estimating locations of electrodes based on a utilizing a system model has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method for modeling a catheter and estimating catheter shapes, the method comprising:
    defining a first model segment and a second model segment corresponding to first and second segments, respectively, of a deformable catheter disposed in a three-dimensional space, each model segment including a segment length and a location along the segment length of a model electrode or model magnetic sensor corresponding to a location of an electrode or magnetic sensor on a corresponding segment of the deformable catheter;
    defining a first variable shape parameter for the first model segment and a second variable shape parameter for the second model segment, wherein the variable shape parameters describe curvatures of the first model segment and second model segment, respectfully;
    varying, with a computer, the first and second variable shape parameters of the first and second model segments to generate a plurality of potential catheter shapes, where each potential catheter shape includes a model electrode location or a model magnetic sensor location;
    obtaining a measured response of an electrode or a magnetic sensor of the deformable catheter while the deformable catheter is disposed in the three-dimensional space;
    updating the variable shape parameters based on the measured response and a model electrode location or model magnetic sensor location from a selected one of the plurality of potential catheter shapes; and
    generating a catheter shape based on the updating of the variable shape parameters and outputting the catheter shape to a display.

2. The method of claim 1, for each segment, further comprising:
    defining a plurality of model electrode locations along the length of at least one of the first and second model segments.

3. The method of claim 1, where defining each of the variable shape parameters comprises:
    defining a curvature and a torsion for each model segment.

4. The method of claim 1, wherein the first model segment and the second model segment are continuous.

5. The method of claim 1, wherein the first variable shape parameter has a first range of curvatures and the second variable shape parameter has a second range of curvatures.

6. The method of claim 1, wherein modeling further comprises, for each model segment, defining a moving frame that follows an arc of the model segment.

7. The method of claim 6, wherein the moving frame comprises a Frenet frame.

8. The method of claim 1, wherein the plurality of catheter shapes are defined in a catheter reference frame.

9. The method of claim 8, further comprising:
transforming the selected one of the plurality of catheter shapes from the catheter reference frame to a reference frame of the three-dimensional space; and
determining a predicted location of the model electrode of the catheter shape in the three-dimensional space.

10. The method of claim 9, further comprising:
generating a predicted impedance response for predicted location of the model electrode in the three-dimensional space.

11. The method of claim 10, wherein the predicted impedance response is utilized with the impedance response of the electrode of the deformable catheter as measured in the three-dimensional space to update the shape parameters.

12. The method of claim 1, wherein the variable shape parameters comprise state variables, wherein varying the variable shape parameters comprises applying a transformation matrix to the state variables.

13. The method of claim 12, wherein a Kalman Filter is used to infer the state variables.

14. The method of claim 12, wherein the plurality of potential catheter shapes comprises a state distribution of potential catheter shapes.

15. The method of claim 14, further comprising:
applying a function to the estimated state distribution to remove unlikely states from the estimated state distribution and generate an updated state distribution.

16. The method of claim 15, wherein the selected one of the plurality of potential catheter shapes comprises a mean of the updated state distribution.

17. The method of claim 1, further comprising:
based on the measured response and a model electrode location or a magnetic sensor location from the selected one the plurality of potential catheter shapes identifying a location of the electrode or the magnetic sensor in the three-dimensional space.

18. The method of claim 1, wherein the updating of the variable shape parameters occurs at least 50 times per second.

19. A system for modeling a catheter and estimating shapes of the catheter, the system including:
a deformable catheter having an electrode and a magnetic sensor;
a medical positioning system to measure responses of the electrode and magnetic sensor in a three-dimensional space;
a processor and memory for storing non-transitory computer readable instruction to:
access a stored definition of first and second model segments corresponding to first and second segments, respectively of the deformable catheter disposed in a three-dimensional space, each model segment including a segment length and a location along the segment length of a model electrode or model magnetic sensor corresponding to a location of an electrode or magnetic sensor of the deformable catheter;
vary a first variable shape parameter for the first model segment and vary a second variable shape parameter for the second model segment, wherein the variable shape parameters describe curvatures of the first model segment and second model segment, respectfully;
generate a plurality of potential catheter shapes based on the varying of the variable shape parameters, where each potential catheter shape includes a model electrode location or model magnetic sensor location for the first and second model segments;
obtain a measured response of an electrode or a magnetic sensor of the deformable catheter while the deformable catheter is disposed in the three-dimensional space;
update the first and second shape parameters based on the measured response and a model electrode location or magnetic sensor location from a selected one of the plurality of potential catheter shapes; and
generate an updated catheter shape based on the update of the first and second shape parameters; and
a display configured to display the updated catheter shape.

20. The system of claim 19, further comprising instructions to identify a location of the electrode or magnetic sensor in the three dimensional space based on the measured response a predicted impedance response for the model electrode location or a predicted magnetic response for the model magnetic sensor location.

* * * * *